United States Patent [19]
Stokker et al.

[11] Patent Number: 5,523,456
[45] Date of Patent: Jun. 4, 1996

[54] INHIBITORS OF FARNESYL-PROTEIN TRANSFERASE

[75] Inventors: Gerald E. Stokker, Gwynedd Valley; Samuel L. Graham, Schwenksville, both of Pa.

[73] Assignee: Merck & Co., Inc., Rahway, N.J.

[21] Appl. No.: 315,046

[22] Filed: Sep. 29, 1994

[51] Int. Cl.$^6$ .................. C07C 317/02; C07C 317/44
[52] U.S. Cl. .................. 560/10; 562/427; 548/495
[58] Field of Search .................. 560/10; 562/427; 548/495

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | De Solms et al. | 514/336 |
| 5,340,828 | 8/1994 | Graham et al. | 514/357 |
| 5,352,705 | 10/1994 | Deana et al. | 514/630 |

FOREIGN PATENT DOCUMENTS

| | | | |
|---|---|---|---|
| 0456180A1 | 11/1991 | European Pat. Off. | C12N 9/10 |
| 0618221A2 | 10/1994 | European Pat. Off. | C07K 5/00 |
| WO91/16340 | 10/1991 | WIPO | C07K 7/06 |

OTHER PUBLICATIONS

Gibbs, J. B. et al., "Selective Inhibition of Farnesyl-Protein Transferase Blocks Ras Processing in Vivo", The Journal of Biological Chemistry, vol. 268, No. 11, pp. 7617–7620 (1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).

James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).

James, G. L. et al., "Benzodiazepine Peptidomimetics: Potent Inhibitors of Ras Farnesylation in Animal Cells", Science, vol. 260, pp. 1937–1942 (1993).

Kohl, N. E. et al. "Selective Inhibiton of ras–Dependent Transformation by a Farnesyltransferase Inhibitors," Science, vol. 260, pp. 1934 14 1937 (1993).

Kohl, N. E. et al., "Protein Farnesyltransferase inhibitors block the growth of ras–dependent tumors in nude mice", Proc. Natl. Acad. Sci. USA, Med. Sciences, vol. 91, pp. 9141–9145 (1994).

Pompliano, D. L. "Steady–State Kinetic Mechanism of Ras Farnesyl:Protein Transferase", Biochemistry, vol. 31, pp. 3800–3807 (1992).

*Primary Examiner*—Paul J. Killos
*Assistant Examiner*—Rosalynd A. Williams
*Attorney, Agent, or Firm*—David A. Muthard; Mark R. Daniel

[57] ABSTRACT

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

23 Claims, No Drawings

000000000000000000000000000000000000000000000000000000

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62:81–88 (1990); Schaber et al., *J. Biol. Chem.*, 265:14701–14704 (1990); Schafer et al., Science, 249:1133–1139 (1990); Manne et al, *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferable: enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732–736 (1991)). Such inhibitors may inhibit while serving as alternate substrates for the Ras farnesyl-transferase enzyme, or may be purely competitive inhibitors (U.S. Pat. No. 5,141, 851, University of Texas).

It has also been demonstrated that certain inhibitors of farnesyl-protein transferase selectively block the processing of Ras oncoprotein intracellularly (N. E. Kohl et al., *Science*, 260:1934–1937 (1993) and G. L. James et al., *Science*, 260:1937–1942 (1993).

Recently, it has been shown that an inhibitor of farnesyl-protein transferase block, the growth of ras-dependent tumors in nude mice (N. E. Kohl et al., *Proc. Natl. Acad. Sci U.S.A.*, 91:9141–9145 (1994).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et al., *J. Antibiotics* 46:222 (1993). In general, deletion of the thiol from a CAAX derivative dramatically reduces the inhibitory potency of these compounds. However, the thiol group potentially places limitations on the therapeutic application of FPTase inhibitors with respect to pharmacokinetics, pharmacodynamics and toxicity. Therefore, a functional replacement for the thiol is desirable. With the exception of the pepticinnamins, non-thiol FPTase inhibitors that are competitive with the Ras substrate have not been described and are the subject of this invention.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenos thiols, and reduced systemic toxicity. Further contained in this invention are chemotherapeutic compositions containing these farnesyl transferase inhibitors and methods for their production.

The compounds of this invention are illustrated by the formulae:

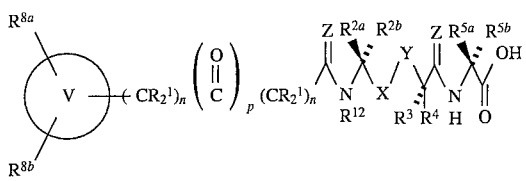

I

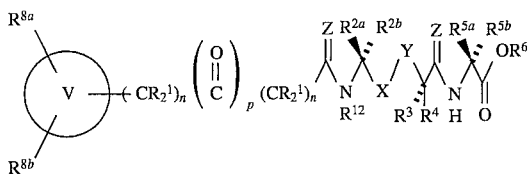

II

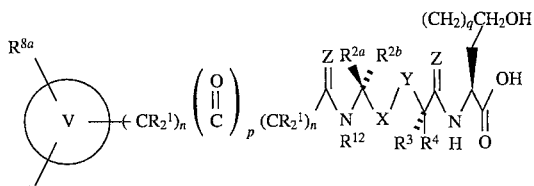

III and

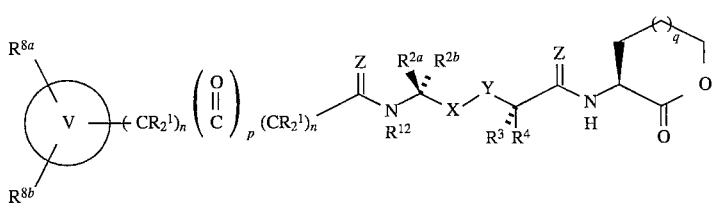

IV

DETAILED DESCRIPTION OF THE INVENTION

The compounds of this invention inhibit the farnesylation of Ras. In a first embodiment of this invention, the Ras farnesyl transferase inhibitors are illustrated by the formula I:

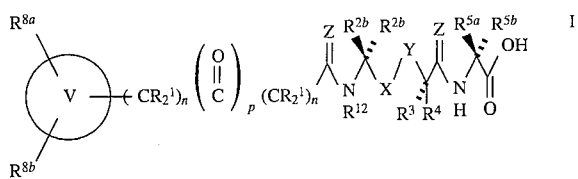

I wherein:
$R^1$ is hydrogen, $C_1$–$C_6$ alkyl or aryl;
$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or
  $R^{2a}$ and $R^{2b}$ are combined to form —$(CH_2)_s$—;
$R^3$ and $R^4$ are independently selected from:
  a) a side chain of a naturally occurring amino acid,
  b) an oxidized form of a side chain of a naturally occurring amino acid which is:
    i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

$R^{5a}$ and $R^{5b}$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}CC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$—wherein one of the carbon atoms is optionally replaced by a moiety selected from: O, $S(O)_m$, —NC(O)—, and —$N(COR^9)$—;

X-Y is a) 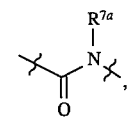

b) 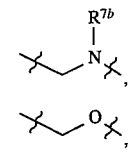

c) 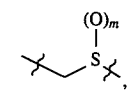

d) 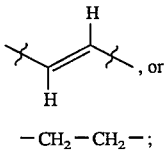

e) , or f) —$CH_2$—$CH_2$—;

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

$R^{7b}$ is selected from a) hydrogen, b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

(V)

is aryl or 1,2,3,4-tetrahydronaphthyl;

Z is independently $H_2$ or O;

m is 0, 1 or 2;

n is independently 0 to 4;

p is 0 or 1; and s is 4 or 5;

or the pharmaceutically acceptable salts thereof.

In a second embodiment of this invention the prodrags of compounds of formula I are illustrated by the formula II:

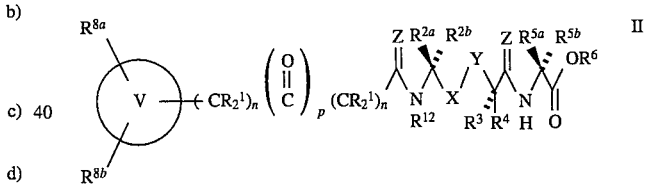

II wherein:

$R^1$ is hydrogen, $C_1$–$C_6$ alkyl or aryl;

$R^{2a}$ and $R^{2b}$ are independently selected from:

a) a side chain of a naturally occurring amino acid, b) an oxided form of a side chain of a naturally occurring amino acid which is:

i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)^2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

$R^{5a}$ and $R^{5b}$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^9)$—;

$R^6$ is a) substituted or unsubstituted $C_1$–$C_8$ alkyl, wherein the substituent or the alkyl is selected from:

1) aryl,
2) heterocycle,
3) —$N(R^{10})_2$,
4) —$OR^9$, or

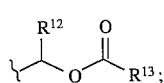  b)

X-Y is

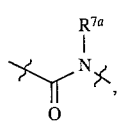  a)

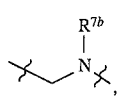  b)

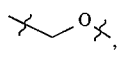  c)

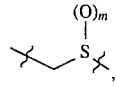  d)

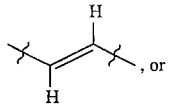  e)

—$CH_2$—$CH_2$—;  f)

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

$R^{7b}$ is selected from a) hydrogen, b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O$—, $R^{10}S(O)_m$—CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

$R^{13}$ is $C_1$–$C_6$ alkyl;

is aryl or 1,2,3,4-tetrahydronaphthyl;

Z is independently $H_2$ or O;

m is 0, 1 or 2;

n is independently 0 to 4;

p is 0 or 1; and s is 4 or 5;

or the pharmaceutically acceptable salts thereof.

In a third embodiment of this invention, the inhibitors of farnesyl transferase are illustrated by the formula III:

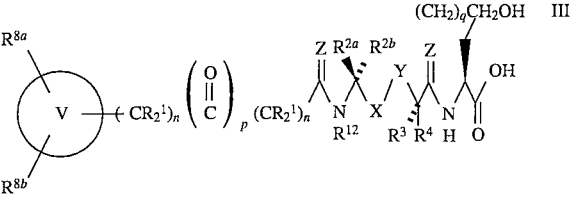

wherein:

$R^1$ is hydrogen, $C_1$—$C_6$ alkyl or aryl;

$R^{2a}$ and $R^{2b}$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O—$, $R^{10}S(O)_m—$, $R^9C(O)NR^9—$, CN, $(R^9)_2N—C(NR^9)—$, $R^9C(O)—$, $R^9OC(O)—$, $N_3$, $—N(R^9)_2$, $R^{10}OC(O)NR^9—$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $—(CH_2)_s—$;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $NO_2$, $R^9O—$, $R^{10}S(O)_m—$, $R^9C(O)NR^9—$, CN, $(R^9)_2N—C(NR^9)—$, $R^9C(O)—$, $R^9OC(O)—$, $N_3$, $—N(R^9)_2$, $R^{10}OC(O)NR^9—$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^3$ and $R^4$ are combined to form $—(CH_2)_s—$;

X-Y is

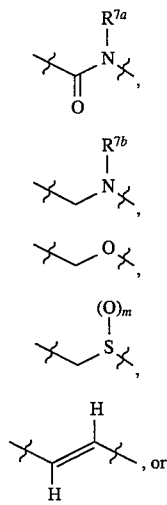

a)

b)

c)

d)

e)

, or f) $-CH_2-CH_2-$;

$R^{7a}$ is selected from a) hydrogen, b) unsubstituted or substituted aryl, c) unsubstituted or substituted heterocycle, d) unsubstituted or substituted cycloalkyl, and e) $C_1-C_6$ alkyl substituted with hydrogen or an unsubstituted or substituted group selected from aryl, heterocycle and cycloalkyl;

$R^{7b}$ is selected from a) hydrogen, b) unsubstituted or substituted aryl, c) unsubstituted or substituted heterocycle, d) unsubstituted or substituted cycloalkyl, e) $C_1-C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O—$, $R^{10}S(O)_m—$, CN, $R^9C(O)NR^9—$, $(R^9)_2N—C(NR^9)—$, $R^9C(O)—$, $R^9OC(O)—$, $N_3$, $—N(R^9)_2$, $R^{10}OC(O)NR^9—$, $C_1-C_{20}$ alkyl, aryl, heterocycle or $C_1-C_{20}$ alkyl substituted with aryl or heterocycle;

$R^9$ is independently selected from hydrogen, $C_1-C_6$ alkyl and aryl;

$R^{10}$ is independently selected from $C_1-C_6$ alkyl and aryl;

$R^{11}$ is independently selected from hydrogen, $C_1-C_6$ alkyl and aryl, provided $R^{11}$ is $C_1-C_6$ alkyl when n is 0;

$R^{12}$ is independently hydrogen or $C_1-C_6$ alkyl;

(V)

is aryl or 1,2,3,4-tetrahydronaphthyl;

Z is independently $H_2$ or O;

m is 0, 1 or 2;

n is independently 0 to 4;

p is 0 or 1;

q is 0, 1 or 2; and s is 4 or 5;

or the pharmaceutically acceptable salts thereof.

In a fourth embodiment of this invention the prodrugs of compounds of formula III are illustrated by the formula IV:

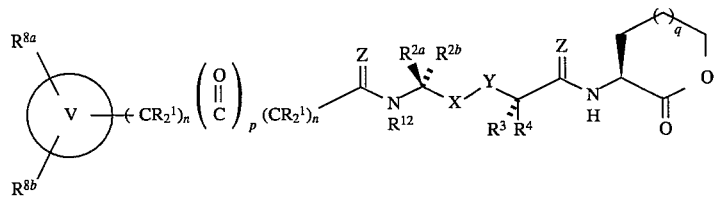

IV wherein:

$R^1$ is hydrogen, $C_1-C_6$ alkyl or aryl;

$R^{2a}$ and $R^{2b}$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $NO_2$, $R^9O-$, $R^{10}S(O)_m-$, $R_9C(O)NR_9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_s-$;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $NO_2$, $R^9O-$, $R^{10}S(O)_m-$, $R^9C(O)NR^9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_s-$;

X-Y is a)

$$\begin{array}{c} R^{7a} \\ | \\ \diagdown\!\!\diagup\!\!\!\!\diagdown_{N}\!\!\diagup \\ \| \\ O \end{array}$$

b)

$$\begin{array}{c} R^{7b} \\ | \\ \diagdown\!\!\diagup\!\!\!\!\diagdown_{N}\!\!\diagup \end{array}$$

c) $\diagdown\!\!\diagup\!\!\!\!\diagdown_{O}\!\!\diagup$, d) $\diagdown\!\!\diagup\!\!\!\!\diagdown_{S}\!\!\diagup^{(O)_m}$, e) $\diagdown\!\!\diagup\!\!\!\!\diagdown\overset{H}{=}\!\!\!\!\diagdown^{H}\!\!\diagup$, or f) $-CH_2-CH_2-$;

$R^{7a}$ is selected from a) hydrogen, b) unsubstituted or substituted aryl, c) unsubstituted or substituted heterocycle, d) unsubstituted or substituted cycloalkyl, and e) $C_1-C_6$ alkyl substituted with hydrogen or an unsubstituted or substitute d group selected from aryl, heterocycle and cycloalkyl;

$R^{7b}$ is selected from a) hydrogen, b) unsubstituted or substituted aryl, c) unsubstituted or substituted heterocycle, d) unsubstituted or substituted cycloalkyl, e) $C_1-C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O-$, $R^{10}S(O)_m-$, CN, $R^9C(O)NR^9-$, $(R^9)_2N-C(NR^9)-$, $R^9C(O)-$, $R^9OC(O)-$, $N_3$, $-N(R^9)_2$, $R^{10}OC(O)NR^9-$, $C_1-C_{20}$ alkyl, aryl, heterocycle or $C_1-C_{20}$ alkyl substituted with aryl or heterocycle;

$R^9$ is independently selected from hydrogen, $C_1-C_6$ alkyl and aryl;

$R^{10}$ is independently selected from $C_1-C_6$ alkyl and aryl;

$R^{11}$ is independently selected from hydrogen, $C_1-C_6$ alkyl and aryl, provided $R^{11}$ is $C_1-C_6$ alkyl when n is 0;

$R^{12}$ is independently hydrogen or $C_1-C_6$ alkyl;

$$\bigcirc\!\!\!\!V$$

is aryl or 1,2,3,4-tetrahydronaphthyl;

Z is independently $H_2$ or O;

m is 0, 1 or 2;

n is independently 0 to 4:

p is 0 or 1;

q is 0, 1 or 2; and s is 4 or 5;

or the pharmaceutically acceptable salts thereof.

In a more preferred embodiment of the invention, the Ras farnesyl transferase inhibitors are illustrated by the formula I:

$$\underset{R^{8b}}{\overset{R^{8a}}{\bigcirc\!\!\!V}}-(CR^1_2)_n\left(\underset{}{\overset{O}{\underset{\|}{C}}}\right)_p(CR^1_2)_n\underset{R^{12}}{N}\overset{Z}{\underset{}{\overset{R^{2b}}{\underset{}{\diagup\!\!\!\diagdown}}\!\!R^{2b}}}\underset{R^3\ R^4}{Y}\overset{Z}{\underset{}{\overset{R^{5a}}{\underset{}{\diagup\!\!\!\diagdown}}\!\!R^{5b}}}\underset{H}{N}\overset{OH}{\underset{O}{\underset{\|}{\diagdown\!\!\!\diagup}}} \quad I$$

wherein:

$R^1$ is hydrogen, $C_1-C_6$ alkyl or aryl;

$R^{2a}$ is selected from:

a) a side chain of a naturally occurring amino acid, wherein the amino acid is selected from alanine, leucine, isoleucine and valine;

b) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^9O-$, $R^{10}S(O)_m-$, $R^9C(O)NR^9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and c) $C_1-C_6$ alkyl substituted with an unsubstituted or substituted group selected from aryl, heterocycle and $C_3-C_{10}$ cycloalkyl; or $R^{2b}$ is hydrogen or $C_1-C_6$ alkyl; or $R^{2a}$ and $R^{2b}$ are combined to form $-(CH_2)_s-$;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1-C_{10}$ alkyl, $C_2-C_{10}$ alkenyl, $C_3-C_{10}$ cycloalkyl, aryl or heterocycle group, wherein the substituent is selected from F, Cl, Br, $NO_2$, $R^9O-$, $R^{10}S(O)_m-$, $R^9C(O)NR^9-$, CN, $(R^9)_2N-$ C(NR$^9$)—, R$^9$C(O)—, R$^9$OC(O)—, N$_3$, —N(R$^9$)$_2$, R$^{10}$OC(O)NR$^9$— and C$_1$–C$_{20}$ alkyl, and d) C$_1$–C$_6$ alkyl substituted with an unsubstituted or substituted group selected from aryl, heterocycle and C$_3$–C$_{10}$ cycloalkyl;

R$^{5a}$ is selected from:
 a) a side chain of a naturally occurring amino acid, wherein the amino acid is selected from methionine and glutamine,
 b) an oxidized form of a side chain of a naturally occurring amino acid which is:
  i) methionine sulfoxide, or
  ii) methionine sulfone,
 c) substituted or unsubstituted C$_1$–C$_{10}$ alkyl, C$_1$–C$_{20}$ alkenyl, C$_3$–C$_{10}$ cycloalkyl, aryl or heterocycle group, wherein the substituent is selected from F, Cl, Br, NO$_2$, R$^9$O—, R$^{10}$S(O)$_m$—, R$^9$C(O)NR$^9$—, CN, (R$^9$)$_2$N—C(NR$^9$)—, R$^9$C(O)—, R$^9$OC(O)—, N$_3$, —N(R$^9$)$_2$, R$^{10}$OC(O)NR$^9$— and C$_1$–C$_{20}$ alkyl, and
 d) C$_1$–C$_6$ alkyl substituted with an unsubstituted or substituted group selected from aryl, heterocycle and C$_3$–C$_{10}$ cycloallyl;

R$^{5b}$ is selected from:
 a) hydrogen, and
 b) C$_1$–C$_3$ alkyl; or

X-Y is

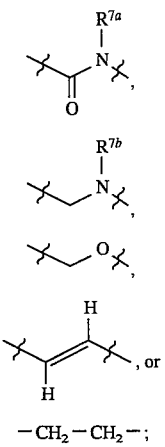

a)

b)

c)

d)

, or e) —CH$_2$—CH$_2$—;

R$^{7a}$ is selected from
 a) hydrogen,
 b) unsubstituted or substituted aryl,
 c) unsubstituted or substituted heterocycle,
 d) unsubstituted or substituted cycloalkyl, and
 e) C$_1$–C$_6$ alkyl substituted with hydrogen or an unsubstituted or substituted group selected from aryl, heterocycle and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^{7b}$ is selected from
 a) hydrogen,
 b) unsubstituted or substituted aryl,
 c) unsubstituted or substituted heterocycle,
 d) unsubstituted or substituted cycloalkyl,
 e) C$_1$–C$_6$ alkyl substituted with hydrogen or an unsubstituted or substituted group selected from aryl, heterocycle and cycloalkyl,
 f) a carbonyl group which is bonded to an unsubstituted or substituted group selected from aryl, heterocycle, cycloalkyl and C$_1$–C$_6$ alkyl substituted with hydrogen or an unsubstituted or substituted group selected from aryl, heterocycle and cycloalkyl, and
 g) a sulfonyl group which is bonded to an unsubstituted or substituted group selected from aryl, heterocycle, cycloalkyl and C$_1$–C$_6$ alkyl substituted with hydrogen or an unsubstituted or substituted group selected from aryl, heterocycle and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^{8a}$ and R$^{8b}$ are independently selected from: hydrogen, F, Cl, Br, NO$_2$, R$^{11}$O—, R$^{10}$S(O)$_m$—, CN, R$^9$C(O)NR$^9$—, (R$^9$)$_2$N—C(NR$^9$)—, R$^9$C(O)—, R$^9$OC(O)—, N$_3$, —N(R$^9$)$_2$, R$^{10}$OC(O)NR$^9$—, C$_1$–C$_{20}$ alkyl, aryl, heterocycle or C$_1$–C$_{20}$ alkyl substituted with aryl or heterocycle;

R$^9$ is independently selected from hydrogen, C$_1$–C$_6$ alkyl and aryl;

R$^{10}$ is independently selected from C$_1$–C$_6$ alkyl and aryl;

R$^{11}$ is independently selected from hydrogen, C$_1$–C$_6$ alkyl and aryl, provided R$^{11}$ is C$_1$–C$_6$ alkyl when n is 0;

R$^{12}$ is independently hydrogen or C$_1$–C$_6$ alkyl;

is aryl or 1,2,3,4-tetrahydronaphthyl;

Z is independently H$_2$ or 0;

m is 0, 1 or 2;

n is independently 0 to 4;

p is 0 or 1; and s is 4 or 5;

or the pharmaceutically acceptable salts thereof.

In a second more preferred embodiment of the invention, the prodrugs of the preferred compounds of the formula I are illustrated by the formula II:

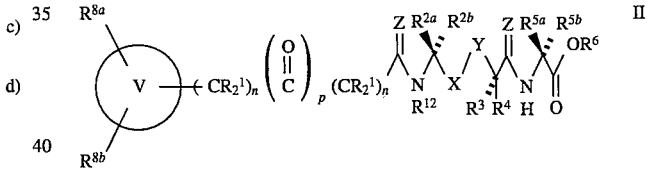

wherein:

R$^1$ is hydrogen, C$_1$–C$_6$ alkyl or aryl;

R$^{2a}$ is selected from:
 a) a side chain of a naturally occurring amino acid, where, in the amino acid is selected from alanine, leucine, isoleucine and valine; and
 b) substituted or unsubstituted C$_1$–C$_{10}$ alkyl, C$_2$–C$_{10}$ alkenyl, C$_3$–C$_{10}$ cycloalkyl, aryl or heterocyclic group, where, in the substituent is selected from F, Cl, Br, NO$_2$, R$^9$O—, R$^{10}$S(O)$_m$—, R$^9$C(O)NR$^9$—, CN, (R$^9$)$_2$N—C(NR$^9$)—, R$^9$C(O)—, R$^9$OC(O)—, N$_3$, —N(R$^9$)$_2$, R$^{10}$OC(O)NR$^9$— and C$_1$–C$_{20}$ alkyl, and
 c) C$_1$–C$_6$ alkyl substituted with an unsubstituted or substituted group selected from aryl, heterocycle and C$_3$–C$_{10}$ cycloalkyl; and R$^{2b}$ is hydrogen or C$_1$–C$_6$ alkyl; or R$^{2a}$ and R$^{2b}$ are combined to form —(CH$_2$)$_s$—;

R$^3$ and R$^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted C$_1$–C$_{10}$ alkyl, C$_2$–C$_{10}$ alkenyl, C$_3$–C$_{10}$ cycloalkyl, aryl or heterocycle group, wherein the substituent is selected from F, Cl, Br, $NO_2$, $R^9O-$, $R^{10}S(O)_m-$, $R^9C(O)NR^9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and d) $C_1-C_6$ alkyl substituted with an unsubstituted or substituted group selected from aryl, heterocycle and $C_3-C_{10}$ cycloalkyl;

$R^{5a}$ is selected from:

a) a side chain of a naturally occurring amino acid, wherein the amino acid is selected from methionine and glutamine, b) an oxidized form of a side chain of a naturally occurring amino acid which is:

i) methionine sulfoxide, or ii) methionine sulfone, c) substituted or unsubstituted $C_1-C_{10}$ alkyl, $C_1-C_{20}$ alkenyl, $C_3-C_{10}$ cycloalkyl, aryl or heterocycle group, wherein the substituent is selected from F, Cl, Br, $NO_2$, $R^9O-$, $R^{10}S(O)_m-$, $R^9C(O)NR^9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and d) $C_1-C_6$ aryl substituted with an unsubstituted or substituted group selected from aryl, heterocycle and $C_3-C_{10}$ cycloalkyl;

$R^{5b}$ is selected from:

a) hydrogen, and b) $C_1-C_3$ alkyl; or $R^6$ is a) substituted or unsubstituted $C_1-C_8$ alkyl, wherein the substituent on the alkyl is selected from:

1) aryl, 2) heterocycle,

3) $-N(R^{10})_2$,

4) $-OR^9$, or b) 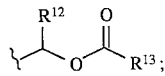

X-Y is a) 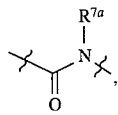

b) 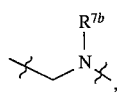

c) 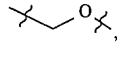

d) 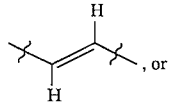, or e) $-CH_2-CH_2-$;

$R^{7a}$ is selected from a) hydrogen, b) unsubstituted or substituted aryl, c) unsubstituted or substituted heterocycle, d) unsubstituted or substituted cycloalkyl, and e) $C_1-C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from a) hydrogen, b) unsubstituted or substituted aryl, c) unsubstituted or substituted heterocycle, d) unsubstituted or substituted cycloalkyl, e) $C_1-C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{8a}$ and $R^{8b}$ are independently selected from: hydrogen, F, Cl, Br, $NO_2$, $R^{11}O-$, $R^{10}S(O)_m-$, CN, $R^9C(O)NR^9-$, $(R^9)_2N-C(NR^9)-$, $R^9C(O)-$, $R^9OC(O)-$, $N_3$, $-N(R^9)_2$, $R^{10}OC(O)NR^9-$, $C_1-C_{20}$ alkyl, aryl, heterocycle or $C_1-C_{20}$ alkyl substituted with aryl or heterocycle;

$R^9$ is independently selected from hydrogen, $C_1-C_6$ alkyl and aryl;

$R^{10}$ is independently selected from $C_1-C_6$ alkyl and aryl;

$R^{11}$ is independently selected from hydrogen, $C_1-C_6$ alkyl and aryl, provided $R^{11}$ is $C_1-C_6$ alkyl when n is 0;

$R^{12}$ is independently hydrogen or $C_1-C_6$ alkyl;

$R^{13}$ is $C_1-C_6$ alkyl;

is aryl or 1,2,3,4-tetrahydronaphthyl;

Z is independently $H_2$ or O;

m is 0, 1 or 2;

n is independently 0 to 4;

p is 0 or 1; and s is 4 or 5;

or the pharmaceutically acceptable salts thereof.

In a third more preferred embodiment of the invention, the inhibitors of farnesyl-protein transferase are illustrated by the formula II:

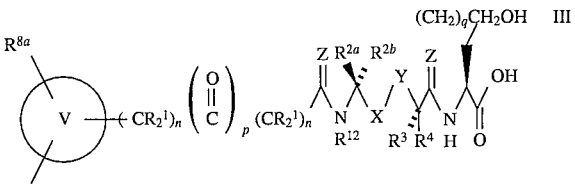

$R^1$ is hydrogen, $C_1-C_6$ alkyl or aryl;

$R^{2a}$ is selected from:

a) a side chain of a naturally occurring amino acid, wherein the amino acid is selected from alanine, leucine, isoleucine and valine;

b) substitute or unsubstituted $C_1-C_{10}$ alkyl, $C_2-C_{10}$ alkenyl, $C_3-C_{10}$ cycloalkyl, aryl or heterocyclic group, whereto the substituent is selected from F, Cl, Br, $NO_2$, $R^9O-$, $R^{10}S(O)_m-$, $R^9C(O)NR^9-$, CN, $(R^9)_2N-C(NR^9)-$, $R^9C(O)-$, $R^9OC(O)-$, $N_3$, $-N(R^9)_2$, $R^{10}OC(O)NR^9-$ and $C_1-C_{20}$ alkyl, and c) $C_1$–$C_6$ alkyl substituted with an unsubstituted or substituted group selected from aryl, heterocycle and $C_3$–$C_{10}$ cycloalkyl; and $R^{2b}$ is hydrogen or $C_1$–$C_6$ alkyl; or $R^{2a}$ and $R^{2b}$ are combined to form —$(CH_2)_s$—;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl;

X-Y is

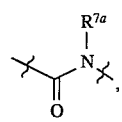 a)

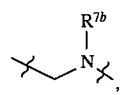 b)

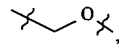 c)

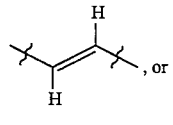 d)

—$CH_2$—$CH_2$—; e)

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

is aryl or 1,2,3,4-tetrahydronaphthyl;

Z is independently $H_2$ or O;

m is 0, 1 or 2;

n is independently 0 to 4;

p is 0 or 1;

q is 0, 1 or 2; and s is 4 or 5;

or the pharmaceutically acceptable salts thereof.

In a fourth more preferred embodiment of the invention, the prodrugs of the preferred compounds of formula III are illustrated by the formula IV:

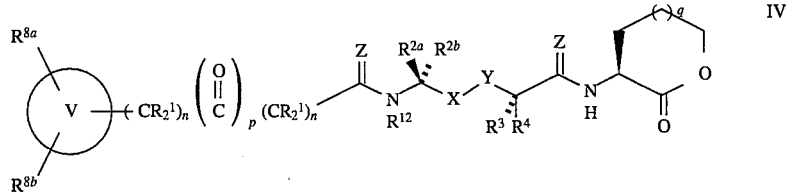 IV wherein:

$R^1$ is hydrogen, $C_1$–$C_6$ alkyl or aryl;

$R^{2a}$ is selected from:

a) a side chain of a naturally occurring amino acid, wherein the amino acid is selected from alanine, leucine, isoleucine and valine;

b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and c) $C_1$–$C_6$ alkyl substituted with an unsubstituted or substituted group selected from aryl, heterocycle and $C_3$–$C_{10}$ cycloalkyl; and $R^{2b}$ is hydrogen or $C_1$–$C_6$ alkyl; or

19

$R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocycle group, where, in the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

X-Y is

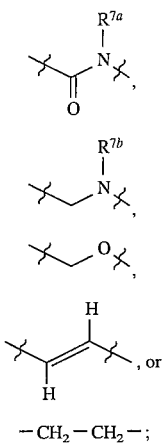

$R^{7a}$ is selected from
  a) hydrogen,
  b) unsubstituted or substituted aryl,
  c) unsubstituted or substituted heterocycle,
  d) unsubstituted or substituted cycloalkyl, and
  e) $C_1$–$C_6$ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
  a) hydrogen,
  b) unsubstituted or substituted aryl,
  c) unsubstituted or substituted heterocycle,
  d) unsubstituted or substituted cycloalkyl,
  e) $C_1$–$C_6$ alkyl substituted with hydrogen or an unsubstituted or substituted group selected from aryl, heterocycle and cycloalkyl,
  f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
  g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

20

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle:

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

is aryl or 1,2,3,4-tetrahydronaphthyl;

Z is independently $H_2$ or O;

m is 0, 1 or 2;

n is independently 0 to 4;

p is 0 or 1;

q is 0, 1 or 2; and s is 4 or 5;

or the pharmaceutically acceptable salts thereof.

The following compounds illustrate the preferred compounds of this invention:

N-{2(S)-[4-(4-nitrophenyl)butanoylamino]-3(S)-methylpentyl}-N-(1-naphthylmethyl)-glycyl-methionine methyl ester N-{2(S)-[5-phenylpentanoylamino]-3(S)-methylpentyl}-N-(1-naphthylmethyl-glycyl-methionine methyl ester N-{2(S)-[4-phenylbenzoylamino]-3(S)-methylpentyl}-N-(1-naphthylmethyl-glycyl-methionine methyl ester N-{2(S)-[5-(2,4-dinitrophenyl)pentanoylamino]- 3(S)-methylpentyl}-N-(1-naphthylmethyl)-glycyl-methionine methyl ester N-{2(S)-[4-nitrobenzoylamino]-3(S)-methylpentyl}-N-(1-naphthylmethyl)-glycyl-methionine methyl ester N-{2(S)-[3-(3-indolyl)propanoylamino}-3(S)-methylpentyl}-N-( 1-naphthylmethyl)-glycyl-methionine methyl ester N-{2(S)-[3-(1-indolyl)propanoylamino}-3(S)-methylpentyl}-N-( 1-naphthylmethyl)-glycyl-methionine methyl ester N-{2(S)-[4-(4-methoxyphenyl)-4-oxobutanoylamino]-4-methylpentyl}-N-(1-naphthylmethyl-glycyl-methionine methyl ester N-{2(S)-{2-(1,2,3,4-tetrahydro)naphthoylamino}-4-methylpentyl}-N( 1-naphthylmethyl)-glycyl-methionine methyl ester N-{2(S)-[1 -(1,2,3,4-tetrahydro)naphthoylamino]-4-methylpentyl}-N( 1-naphthylmethyl-glycyl-methionine methyl ester N-{2(S)-[4-(4-hydroxyphenyl)butanoylamino]-4-methylpentyl}-N-( 1-naphthylmethyl)-glycyl-methionine methyl ester N-{2(S)-[4-(4-aminophenyl)butanoylamino]-4-methylpentyl}-N-( 1-naphthylmethyl)-glycyl-methionine methyl ester N-{2(S)-[2-benzylbenzoylamino]-4-methylpentyl}-N-(1-naphthylmethyl)-glycyl-methionine methyl ester N-{2(S)-[(2-benzoylphenyl)acetylamino]-4-methylpentyl}-N-( 1-naphthylmethyl)-glycyl-methionine methyl ester N-{2(S)-[(2-benzylphenyl)acetylamino]-4-methylpentyl}-N-( 1-naphthylmethyl)-glycyl-methionine methyl ester N-{2(S)-[(4-benzylphenyl)acetylamino]-4-methylpentyl}-N-( 1-naphthylmethyl)-glycyl-methionine methyl ester N-{2(S)-[(3-benzoylphenyl)acetylamino]-4-methylpentyl}-N-( 1-naphthylmethyl)-glycyl-methionine methyl ester
N-{2(S)-[4-(4-nitrophenyl)butanoylamino]-3(S)-methylpentyl}-N-( 1-naphthylmethyl)-glycyl-methionine
N-{2(S)-[5-phenylpentanoylamino]-3(S)-methylpentyl}-N-( 1-naphthylmethyl)-glycyl-methionine
N-{2(S)-[4-phenylbenzoylamino]-3(S)-methylpentyl}-N-(1-naphthylmethyl)-glycyl-methionine
N-{2(S)-[5-(2,4-dinitrophenyl)pentanoylamino]- 3(S)-methylpentyl}-N-(1-naphthylmethyl)-glycyl-methionine
N-{2(S)-[4-nitrobenzoylamino]-3(S)-methylpentyl}-N-(1-naphthylmethyl)-glycyl-methionine
N-{2(S)-[3-(3-indolyl)propanoylamino]-3(S)-methylpentyl}-N-( 1-naphthylmethyl)-glycyl-methionine
N-{2(S)-[3-(1-indolyl)propanoylamino]-3(S)-methylpentyl}-N-( 1-naphthylmethyl)-glycyl-methionine
N-{2(S)-[4-(4-methoxyphenyl)-4-oxobutanoylamino]-4-methylpentyl}-N-( 1-naphthylmethyl)-glycyl-methionine
N-{2(S)-[2-(1,2,3,4-tetrahydro)naphthoylamino]- 4-methylpentyl}-N(1-naphthylmethyl)-glycyl-methionine
N-{2(S)-[1-(1,2,3,4-tetrahydro)naphthoylamino]- 4-methylpentyl}-N(1-naphthylmethyl)-glycyl-methionine
N-{2(S)-[4-(4-nitrophenyl)butanoylamino]- 4-methylpentyl}-N-(1-naphthylmethyl)-glycyl-methionine
N-{2(S)-[4-(4-hydroxyphenyl)butanoylamino]- 4-methylpentyl}-N-(1-naphthylmethyl)-glycyl-methionine
N-{2(S)-[(3-benzoylphenyl)acetylamino]- 4-methylpentyl}-N-(1-naphthylmethyl)-glycyl-methionine
N-{2(S)-[4-(4-aminophenyl)butanoylamino]-4-methylpentyl}-N-( 1-naphthylmethyl)-glycyl-methionine
N-{2(S)-[2-benzylbenzoylamino]-4-methylpentyl}-N-(1-naphthylmethyl)-glycyl-methionine
N-{2(S)-[(2-benzoylphenyl)acetylamino]-4-methylpentyl}-N-( 1-naphthylmethyl)-glycyl-methionine
N-{2(S)-[(2-benzylphenyl)acetylamino]-4-methylpentyl}-N-( 1-naphthylmethyl)-glycyl-methionine
N-{2(S)-[(4-benzylphenyl)acetylamino]-4-methylpentyl}-N-( 1-naphthylmethyl)-glycyl-methionine
or the pharmaceutically acceptable salts thereof.

The most preferred compounds of the invention are:
N-{2(S)-[4-(4-nitrophenyl)butanoylamino]-3(S)-methylpentyl}-N-( 1-naphthylmethyl)-glycyl-methionine

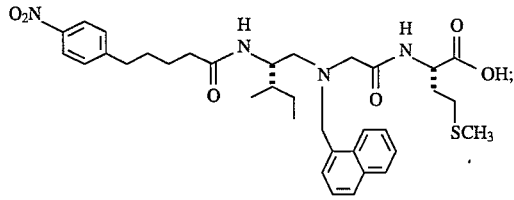

N-{2(S)-[4-(4-nitrophenyl)butanoylamino]-3(S)-methylpentyl}-N-( 1-naphthylmethyl)-glycyl-methionine methyl ester

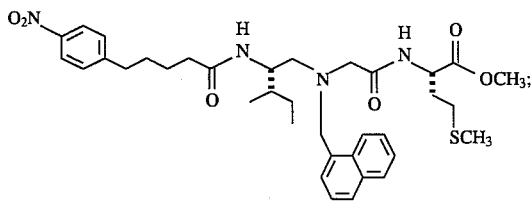

N-{2(S)-[5-(2,4-dinitrophenyl)pentanoylamino]- 3(S)-methylpentyl}-N(1-naphthylmethyl)-glycyl-methionine

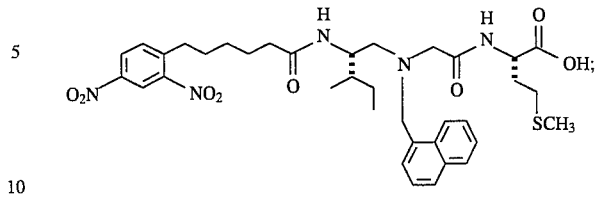

N-{2(S)-[5-(2,4-dinitrophenyl)pentanoylamino]- 3(S)-methylpentyl}-N(1-naphthylmethyl)-glycyl-methionine methyl ester

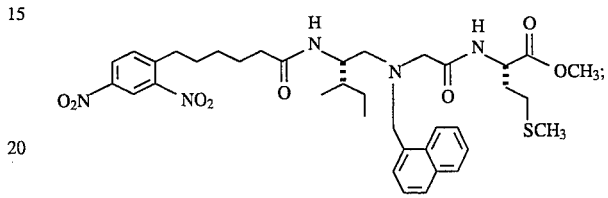

or the pharmaceutically acceptable salts thereof.

In the present invention, the amino acids which are disclosed are identified both by conventional 3 letter and single letter abbreviations as indicated below:

| Alanine | Ala | A |
| --- | --- | --- |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used heroin, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ting is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzisoxazolyl, chromanyl, cinnolinyl, dihydrobenzofuryl, dihydro-benzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$— and $C_1-C_{20}$ alkyl.

When $R^{2a}$ and $R^{2b}$ and $R^3$ and $R^4$ are combined to form —$(CH_2)_s$—, cyclic moieties are formed. Examples of such cyclic moieties include, but are not limited to:

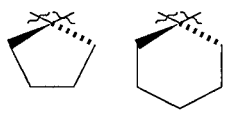

When $R^{5a}$ and $R^{5b}$ are combined to form —$(CH_2)_s$—, cyclic moieties as described herein above for $R^{2a}$ and $R^{2b}$ and $R^3$ and $R^4$ are formed. In addition, such cyclic moieties may optionally include a heteroatom(s). Examples of such heteroatom-containing cyclic moieties include, but are not limited to:

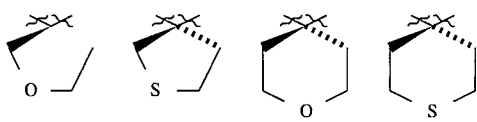

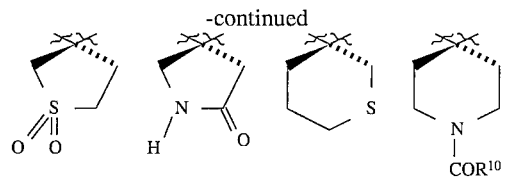

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^1$, Z, n, etc.) at a particular location in a molecule be independent of its definitions elsewhere in that molecule. Thus, —$N(R^1)_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| $Et_3N$ | Triethylamine; |
| EtOAc | Ethyl acetate; |
| FAB | Fast atom bombardment; |
| HOOBT | 3-Hydroxy-1,2,2-benzotriazin-4(3H)-one; |

| | |
|---|---|
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A-J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

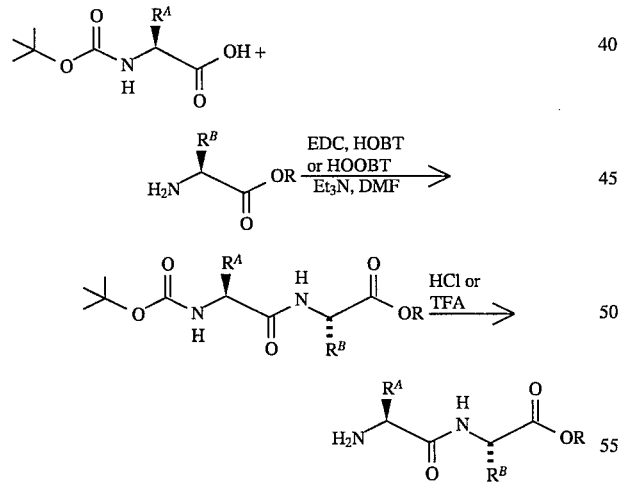

REACTION SCHEME B
Reaction B. Preparation of reduced peptide subunits by reductive alkylation

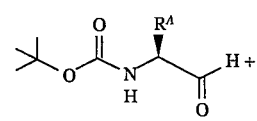

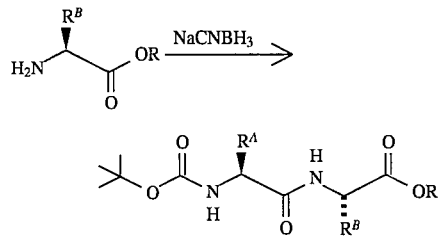

REACTION SCHEME C
Reaction C. Alkylation/reductive alkylation of reduced peptide subunits

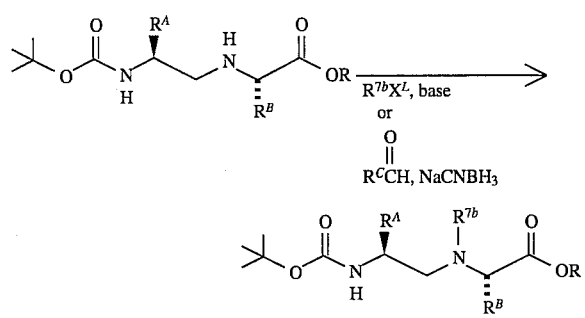

REACTION SCHEME D
Reaction D. Coupling of residues to form an amide bond

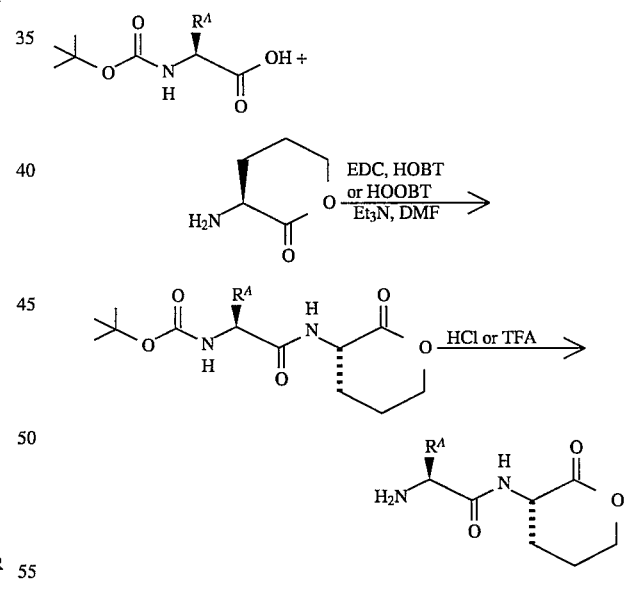

REACTION SCHEME E
Reaction E. Preparation or reduced dipeptides from peptides

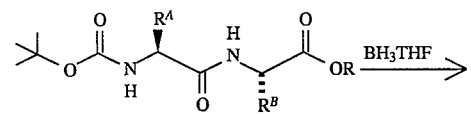

REACTION SCHEME E -continued
Reaction E. Preparation or reduced dipeptides from peptides

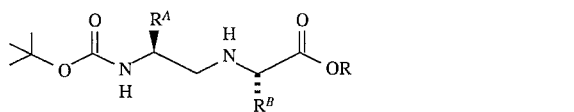

where $R^A$ and $R^B$ are $R^{2a}$, $R^{2b}$, $R^3$, $R^4$, $R^{5a}$ or $R^{5b}$ as previously defined; $X^L$ is a leaving group, e.g., Br—, I— or MsO—; and $R^C$ is defined such that $R^{7b}$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme F. Step B, Part 1), and stereospecific boron triflouride or zinc chloride activated organo-magnesio, organo-lithio, or organo-zinc copper(1) cyanide $S_N2'$ displacement reaction (Scheme F, Step G). Through the use of optically pure N-Boc amino acids as starting material and these two key reactions, the stereo-chemistry of the final products is well defined. In Step H of Scheme F, the amino terminus substituent $R^x$ is incorporated using coupling reaction A and $R^xCOOH$; the alkylation reaction C using $R^xCHO$ and a reducing agent; or alkylation reaction C using $R^xCH_2X^L$.

The alkane analogs are prepared in a similar manner by including an additional catalytic hydrogenation step as outlined in Reaction Scheme G.

REACTION SCHEME F

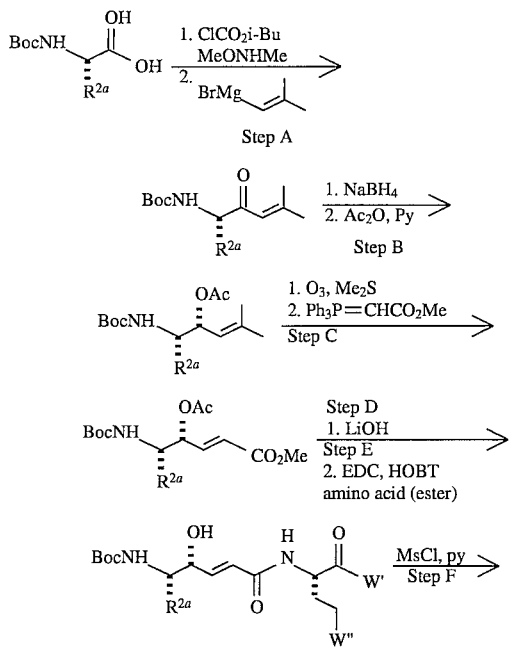

REACTION SCHEME F -continued

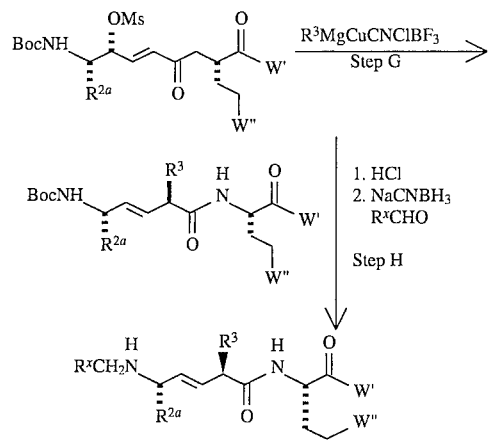

wherein:

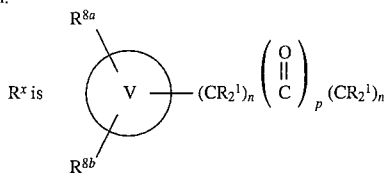

$R^x$ is

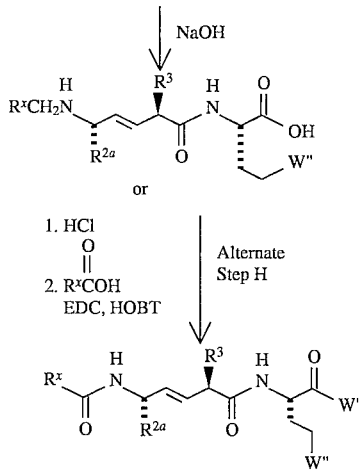

$W' = OMe$, $W'' = SMe$
$W' - W'' = O$

REACTION SCHEME G

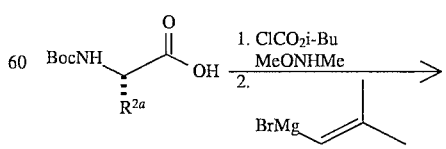

-continued
REACTION SCHEME G

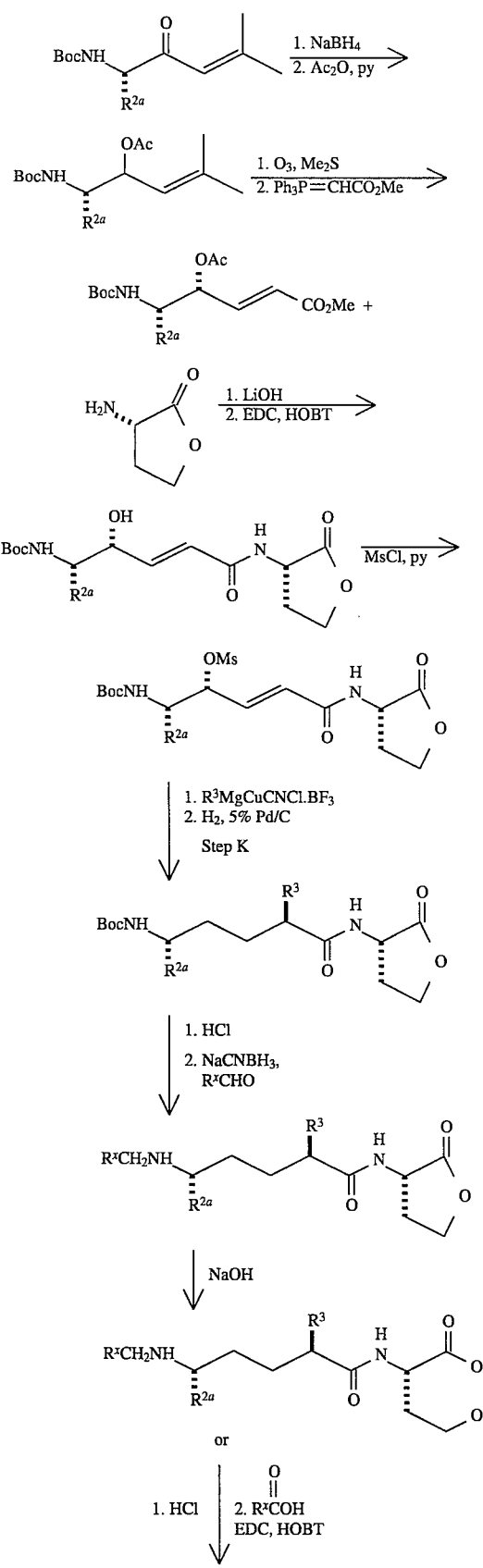

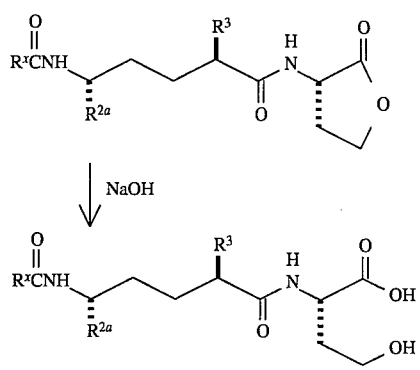

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. The N-Boc derivative 4 is then obtained by the treatment of 3 with BOC anhydride and DMAP (4-dimethylaminopyridine) in methylene chloride. Alkylation of 4 with-$R^3 X^L$, where $X^L$ is a leaving group such as Br—, I— or Cl— in THF/DME (1,2-dimethoxyethane) in the presence of a suitable base, preferably NaHMDS [sodium bis(trimethylsilyl)amide], affords 5, which is retreated with NaHMDS followed by either protonation or the addition of an alkyl halide $R^4 X$ to give 6a or 6b, respectively. Alternatively, 6a can be prepared from 4 via an aldol condensation approach. Namely, deprotonation of 4 with NaHMDS followed by the addition of a carbonyl compound $R^y R^z CO$ gives the adduct 7 Dehydration of 7 can be effected by mesylation and subsequent elimination catalyzed by DBU (1,8-diazabicyclo[5.4.0]undec7-ene) or the direct treatment of 7 with phosphorus oxychloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. The peptide coupling of acid 9b with either an alpha-aminolactone (e.g., homoserine lactone, etc.) or the ester of an amino acid is carried out under the conditions exemplified in the previously described references to yield derivative 10. Treatment of 10 with gaseous hydrogen chloride gives 11, which undergoes reductive alkylation in the presence of an aldehyde $R^x CHO$ (12) and a reducing agent (e.g., sodium cyanoboro-hydride); or acylation in the presence of $R^x COOH$ (13) and a peptide coupling reagent affording the products 14a and b. It is understood that $R^x CHO$ and $R^x COOH$ reagents are readily available commercially or may be readily prepared by techniqes well known in the an from commercially available starting materials. Hydrolysis of compounds 14 to the corresponding hydroxy acids and acids, respectively, is accomplished by standard methods such as treatment with NaOH in alcoholic or aqueous milieux followed by careful acidification with dilute HCl.

SCHEME H

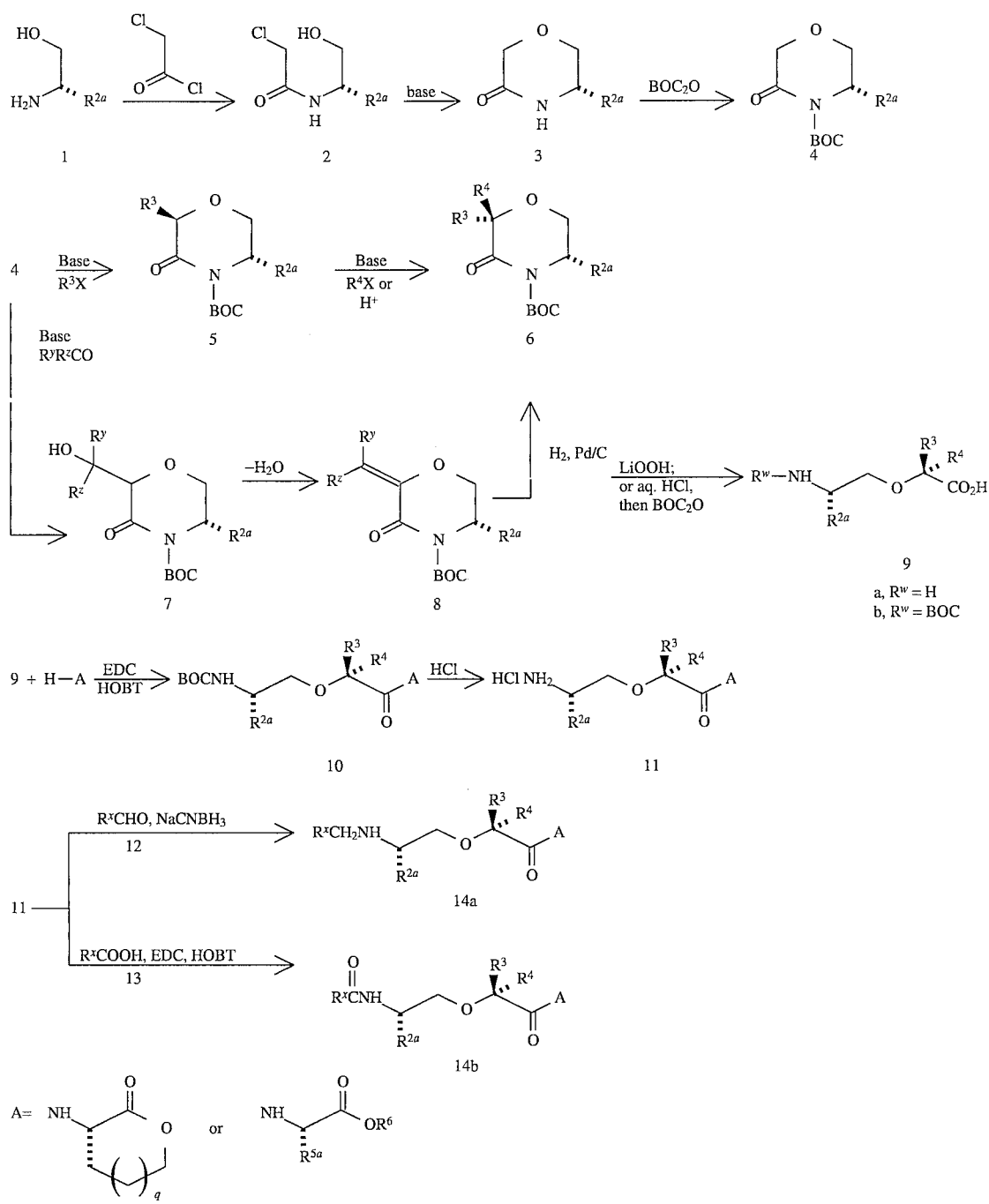

The thia, oxothia and dioxothia isostere compounds of this invention are prepared in accordance to the route depicted in Scheme I. Aminoalcohol 1 is derivatized with BOC₂O to give 15. Mesylation of 15 followed by reaction with methyl alpha-mercaptoacetate in the presence of cesium carbonate gives sulfide 16. Removal of the BOC group in 16 with TFA followed by neutralization with di-isopropylethylamine leads to lactam 17. N-BOC derivative 18 is obtained via the reaction of 17 with BOC anhydride in THF catalyzed by DMAP. Sequential alkylation of 18 with the alkyl halides R³X and R⁴X in THF/DME using NaHDMS as the deprotonation reagent produces 19. Hydrolysis of 19 in hydro-chloride to yield 20a, which is derivatized with Boc anhydride, to yield 20b. The coupling of 20b with an alpha-aminolactone (e.g., homoserine lactone, etc.) or the ester of an amino acid is carded out under conventional conditions as exemplified in the previously described references to afford 21. Sulfide 21 is readily oxidized to sulfone 22 by the use of MCPBA (m-chloroperoxybenzoic acid). The N-BOG group of either 21 or 22 is readily removed by treatment with gaseous hydrogen chloride. The resultant amine hydrochloride 23 undergoes reductive alkylation in the presence of an aldehyde R¹CHO (12) and a reducing agent (e.g., sodium cyanoborohydride); or acylation in the presence of R¹COOH (13) and a peptide coupling reagent to afford the products 24 and 25.

treatment of cancer. Examples of the type of cancer which may be treated with the compounds of this invention

SCHEME I

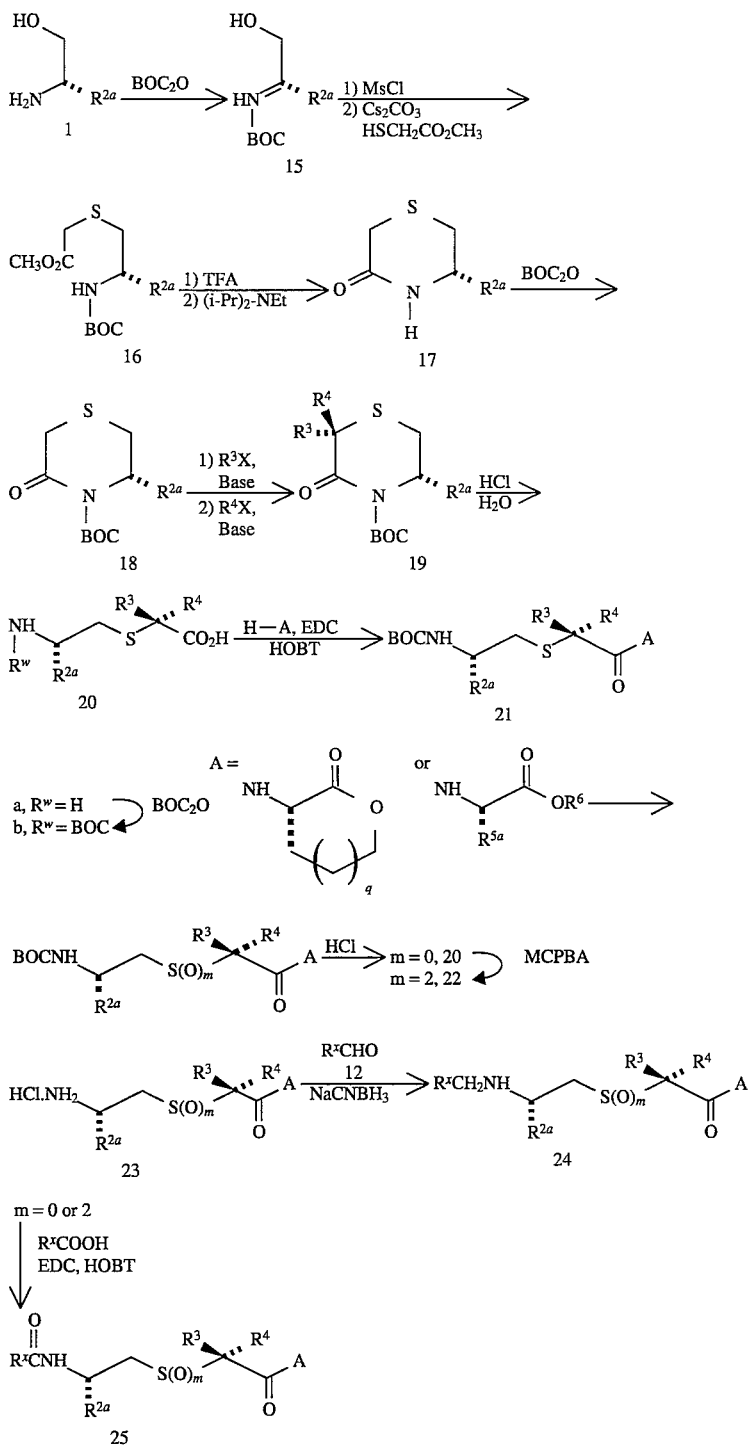

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially; smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention s and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

Preparation of

N-{2(S)-[4-(4-nitrophenyl)butanoylamino]- 3(S)-methylpentyl}-N-( 1-naphthylmethyl)-glycyl-methionine methyl ester Step A: Preparation of
N-(2(S)-(t-butoxycarbonylamino)-
3(S)-methylpentyl)glycine methyl ester Glycine methyl ester hydrochloride (4.41 g, 0.035 mol) was dissolved in 1,2-dichloroethane (50 mL) and DMF (5 mL) and treated with 3A molecular sieves (10 g) and N-t-butoxycarbonyl-isoleucinal (6.3 g, 0.029 mol) with stirring at 0° C. Sodium triacetoxyborohydride (9.27 g, 0.044 mol) was added, and the pH of the mixture was adjusted to 6 with triethylamine (3 mL, 0.022 mol). After stirring for 18 h the mixture was filtered, concentrated to a small volume and partitioned between EtOAc and water. The aqueous layer was extracted with EtOAc (2×50 mL). The combined organic phase was washed with aqueous saturated NaHCO$_3$ solution, brine, and dried (Na$_2$SO$_4$). Filtration and concentration afforded a residue which was purified by flash chromatography (SiO$_2$, EtOAc:hexane, 1:3) to give the title compound.

$^1$H NMR (CDCl$_3$) δ4.69 (1H, m), 3.72 (3H, s), 3.48–3.62 (1H, m), 3.42 (2H, ABq), 2.65 (2H, d, J=6 Hz), 1.4–1.6 (2H, m), 1.48 (9H, s), 1.04–1.2 (1H, m), 0.85–0.295 (6H, m) ppm.

Step B: Preparation of
N-[2(S)-(t-Butoxycarbonylamino)-
3(S)-methylpentyl]-N-(1-naphthylmethyl)glycine
methyl ester N-[2(S)-(t-Butoxycarbonylamino)-3(S)-methylpentyl] glycine methyl ester (2.00 g, 6.97 mmol) was dissolved in 1,2-dichloroethane (56 ml) and 3A molecular sieves were added followed by 1-naphthaldehyde (1.89 ml, 13.9 mmol) and sodium triacetoxyborohydride (665 g, 31.4 mmol). The mixture was stirred at ambient temperature for 16 h, and filtered through glass fiber paper and concentrated. The residue was partitioned between EtOAc and sat. NaHCO$_3$ (100 ml/25 ml). The aqueous layer was extracted with EtOAc (3×50 ml). The organic layers were combined, dried (Na$_2$SO$_4$), filtered, and Concentrated to give 5.0 g of crude product which was purified by chromatography (SiO$_2$, 15–33% ethyl acetate/hexane) to give the title compound.

$^1$H NMR (CD$_3$OD) δ8.44–8.38 (1H, d, J=6Hz), 7.88–7.77 (2H, m,), 7.55–7.35 (4H, m), 6.34–6.27 (1H, m), 4.25 (2H, ABq), 3.66 (3H, s), 3.40–3.23 (1H, m), 2.90 (1H, dd, J=6 and 15Hz), 2.63 (1H, dd, J=6 and 15Hz), 1.57–1.46 (1H, m), 1.43 (9H, s), 1.34–1.18 (2H, m), 1.06–0.85 (1H, m) and 0.85–0.71 (6H, m) ppm.

Step C Preparation of
N-[2(S)-(t-Butoxycarbonylamino)-
3(S)-methylpentyl]-N-(1-naphthylmethyl)glycine N-[2(S)-(t-Butoxycarbonylamino)-3(S)-methylpentyl]-N-(1-naphthylmethyl)glycine methyl ester (2.61 g, 6.10 mmol) was dissolved in MeOH (50 ml) and 1N NaOH (24.4 ml, 24.4 mmol) was added. The mixture was stirred at ambient temperature for 4 h and concentrated. The resulting residue was dissolved in water (25 ml) and neutralized with 1N HCl (24.4 ml). The aqueous layer was washed with EtOAc (3×50 ml). The organic layers were combined, dried with Na$_2$SO$_4$, filtered, and concentrated to give the product. $^1$H NMR (CD$_3$OD) δ8.43 (1H, d, J=6Hz), 7.97 (2H, t, J=6 Hz) 7.75–7.48 (4H, m), 4.96 (1H, d, J=12Hz), 4.72 (1H, d, J=12 Hz), 3.80–3.58 (3H, m), 3.49–3.40 (1H, dd,, J=3 and 12 Hz), 3.03 (1H, dd, J=3 and 12 Hz), 1.42 (9H, s,), 1.37–1.28 (2H, m), 1.80–1.00 (1H, m), 0.94–0.78 (6H, m,) ppm.

Step D: Preparation of
N-[2(S)-(t-Butoxycarbonylamino)-
3(S)-methylpentyl]-N-(1-naphthylmethyl)
glycine-methionine methyl ester N-[2(S)-(t-Butoxycarbonylamino)-3(S)-methylpentyl]-N-(1-naphthylmethyl)glycine (2.29 g, 5.53 mmol), dissolved in DMF (20 mL), was treated with HOBT (0.822 g, 6.08 mmol), EDC (1.17 g, 6.08 mmol), and methionine methyl ester hydrochloride (1.21 g, 6.08 mmol). The pH was adjusted to 7.5 with Et$_3$N (1.7 mL, 12 mmol) and the mixture was stirred at ambient temperature for 24 h. The mixture was concentrated, and the residue was partitioned between EtOAc (50 mL) and saturated NaHCO$_3$ solution (25 mL). The aqueous layer was extracted with EtOAc (1×30 mL). The organic layers were combined, washed with brine (1×25 mL), dried (Na$_2$SO$_4$), filtered, and concentrated to give 3.2 g of crude product which was purified by chromatography (silica gel eluting with 1:3 to 1:2 ethyl acetate in hexane) to give pure product. $^1$H NMR (CD$_3$OD) δ8.33 (1H, d, J=6 Hz), 7.90 (1H, d, J=6 Hz), 7.82 (1H, d, J=6 Hz), 7.61–7.39 (4H, m), 6.60–6.52 (1H, m), 4.32–4.06 (2H, m), 3.90–3.69 (1H, m), 3.65 (3H, s), 3.27–3.14 (2H, m), 2.93–2.70 (2H, m), 2.19–1.78 (6H, m), 1.63–1.30 (13H, m), 1.19–1.05 (1H, m), 0.95–0.81 (6H, m) ppm.

Step E: Preparation of
N-(2(S)-amino-3(S)-methylpentyl)-N-
(1-naphthylmethyl)-glycyl-methionine methyl ester
hydrochloride N-[2(S)-(t-Butoxycarbonylamino)-3(S)-methylpentyl]-N-( 1-naphthylmethyl)-glycyl-methionine methyl ester (2.82 g, 5.04 mmol) was dissolved in EtOAc (50 mL) and cooled to −25° C. HCl was bubbled through the mixture until TLC (95:5 CH$_2$Cl$_2$:MeOH) indicated complete reaction. Nitrogen was bubbled through the mixture to remove excess HCl and the mixture was then concentrated to give the title compound. $^1$H NMR (CD$_3$OD) d 8.31 (1H, d, J=6 Hz), 7.96 (2H, d, J=6 Hz), 7.83–7.71 (1H, m), 7.68–7.49 (3H, m), 4.76–4.55 (4H, m), 3.84–3.75 (2H, m), 3.71 (3H, s), 3.70–3.59 (1H, m), 3.21–3.00 (2H, m), 2.57–2.38 (3H, m), 217–2.04 (4H, m), 1.97–1.81 (1H, m), 1.63–1.50 (1H, m), 1.39–1.20 (1H, m), 1.19–1.00 (1H, m), 0.95–0.79 (6H, m) ppm.

Step F: N-{2(S)-[4-(4-nitrophenyl)butanoylamino]-
3(S)-methylpentyl}-N-(1-naphthylmethyl)-glycyl-
methionine methyl ester 4-(4-Nitrophenyl)butyric acid (73 mg, 350 μmol), dissolved in DMF (5 ml) was treated with HOBT (60 mg, 350 μmol), EDC (76 mg, 350 μmol) and N-[2(S)-amino-3-methylpentyl)-N-(1-naphthylmethyl)-glycyl-methionine methyl ester hydrochloride (160 mg, 300 μmol). The pH was adjusted to ~7.5 with Et$_3$N (170 μl, 385 μmol) and the mixture was stirred at ambient temperature for 16 h. The mixture was concentrated and the residue was partitioned between EtOAc (100 ml) and H$_2$O (100 ml). The organic layer was washed with H$_2$O (2×50 ml), dried (MgSO$_4$), filtered and concentrated to give a crude product which was purified by chromatography (silica gel, eluting with 1:1 to 1:2 hexane: EtOAc) to give the title compound.

Step G: Preparation:of
N-{2(S)-[4-( 4-nitrophenyl)butanoylamino]-3(S)-methyl-
pentyl}-N-(1-naphthylmethyl)-glycyl-methionine The methyl ester from Step F (87 mg, 130 μmol) was dissolved in MeOH (1 ml) and 1.00N NaOH (300 μl, 300 μmol) was added. The mixture was stirred at 45° C. under argon for 45 minutes, then the solution was partitioned between EtOAc (100 ml) and 5% citric acid (50 ml). The organic layer was washed with H$_2$O (2×50 ml), dried (MgSO$_4$), filtered and evaporated to give the title compound.

Anal. Calcd for C$_{34}$H$_{44}$N$_4$O$_6$S: C, 64.13; H, 6.96; N, 8.80. Found: C, 64.31; H, 7.07: N, 8.70.

Example 2

The following compounds were prepared using the procedure described for Example 1, Step F, but substituting 4-(4-nitrophenyl)butyric acid with the appropriate acid.

N-{2(S)-[5-phenylpentanoylamino]-3(S)-methylpentyl}-N-( 1-naphthylmethyl-glycyl-methionine methyl ester N-{2(S)-[4-phenylbenzoylamino]-3(S)-methylpentyl}-N-(1-naphthylmethyl-glycyl-methionine methyl ester Anal. Calcd. for C$_{38}$H$_{45}$N$_3$O$_4$S C, 71.33 :H, 7.09 : N, 6.57 C. 71.09: H, 7.07. N, 6.77

Fab mass spectrum m/z=640 (M+1 )

N-{2(S)-[5-(2,4-dinitrophenyl)pentanoylamino]- 3(S)-methylpentyl}-N-(1-naphthylmethyl)-glycyl-methionine methyl ester Anal. Calcd. for C$_{36}$H$_{47}$N$_5$O$_8$S •1.7 CF$_3$CO$_2$H C, 52.36: H, 5.43: N, 7.75 C, 52.38:H, 5.49: N, 7.80

Fab mass spectrum m/z=710 (M+1)

N-{2(S)- [4-nitrobenzoylamino]-3(S)-methylpentyl}-N-(1-naphthylmethyl)-glycyl-methionine methyl ester Anal. Calcd. for C$_{32}$H$_{40}$N$_4$O$_6$S•0.3 EtOAc C, 62.77 :H, 6.73: N, 8.82 C, 62.41 :H, 6.51 : N, 8.96

39

N-{2(S)-[3-(3-indolyl)propanoylamino}-3(S)-methylpentyl}-N-( 1-naphthylmethyl)-glycyl-methionine methyl ester
Anal. Calcd. for $C_{36}H_{46}N_4O_4S$•1.6 $CF_3CO_2H$ C, 57.89: H, 5.90: : N, 6.89 C, 57.94 :H, 5.96 : N, 6.83

N-{2(S)-[3-(1-indolyl)propanoylamino}-3(S)-methylpentyl}-N-( 1-naphthylmethyl)-glycyl-methionine methyl ester
Anal. Calcd. for $C_{36}H_{46}N_4O_4S$•1.65 $CF_3CO_2H$ C, 57.63: H, 5.86: N, 6.84 C, 57.73: H, 5.94: N, 6.82

Example 3

The following compounds were prepared using the procedure described for Example 1. Step G but substituting the methyl ester used therein with the corresponding methyl ester from Example 2.

N-{2(S)-[5-phenylpentanoylamino]-3(S)-methylpentyl}-N-( 1-naphthylmethyl)-glycyl-methionine
Anal. Calcd. for $C_{35}H_{47}N_3O_4S$•0.35 $CHCl_3$ C, 65.56 :H, 7.37 : N, 6.49 C, 65.59 :H, 7.37 : N, 6.68

N-{2(S)-[4-phenylbenzoylamino]-3(S)-methylpentyl}-N-(1-naphthylmethyl)-glycyl-methionine
Anal. Calcd. for $C_{37}H_{43}N_3O_4S$•0.75 EtOAc C, 69.43 :H, 7.14: N, 6.07 C, 69.52: H, 7.05: N, 5.87

N-{2(S)-[5-(2,4-dinitrophenyl)pentanoylamino]- 3(S)-methylpentyl}-N-(1-naphthylmethyl)-glycyl-methionine
Anal. Calcd. for $C_{35}H_{45}N_5O_8S$•1.0 EtOAc C, 59.75: H, 6.81: N, 8.93 C, 59.97: H, 6.57: N, 8.59

N-{2(S)-[4-nitrobenzoylamino]-3(S)-methylpentyl}-N-(1-naphthylmethyl)-glycyl-methionine
Anal. Calcd. for $C_{31}H_{38}N_4O_6S$•0.45 EtOAc C, 62.10:H, 6.61 : N, 8.83 C, 61.71: H, 6.37 : N, 9.16

N-{2(S)-[3-(3-indolyl)propanoylamino]-3(S)-methylpentyl}-N-( 1-naphthylmethyl)-glycyl-methionine
Anal. Calcd. for $C_{35}H_{44}N_4O_4S$•0.4 EtOAc. 0.75 $H_2O$ C, 66.04 : H, 7.38 : N, 8.42 C, 66.03 :H, 7.15 : N, 8.41

N-{2(S)-[3-(1-indolyl)propanoylamino]-3(S)-methylpentyl}-N-( 1-naphthylmethyl)-glycyl-methionine
Anal. Calcd. for $C_{35}H_{44}N_4O_4S$•0.8 EtOAc •0.85 $H_2O$ C, 65.30 :H, 7.47 : N, 7.97 C, 65.26 :H, 7.11 :N, 7.97

Example 4

Preparation of
N-{2(S)-[4-(4-methoxyphenyl)-4-oxobutanoylamino]-4-methylpentyl}-N-(1-naphthylmethyl-glycyl-methionine methyl ester Step A. Preparation of
N-(2(S)-amino-4-methylpentyl)-N-(1-naphthylmethyl)-glycyl-methionine methyl ester hydrochloride Using the methods of Example 1, Steps A-E, substituting N-t-butoxycarbonyl-leucinal for the N-t-butoxycarbonyl-isoleucinal used therein, the title compound was obtained.

Step B. Preparation of
N-{2(S)-[4-(4-methoxyphenyl)-4-oxobutanoylamino]-4-methylpentyl}-N-(1-naphthylmethyl-glycyl-methionine methyl ester Using the method of Example 1, Step F and the appropriate carboxylic acid, the product of step A was converted to the title compound.

40

Anal. Calcd. for $C_{36}H_{47}N_3O_6S$•1.8 $CF_3CO_2H$•0.45 $H_2O$: C, 55.10: H, 5.80: N, 4.87 Found: C, 55.10: H, 5.8(}: N, 4.96
Fab mass spectrum m/z=650 (M+1)

Example 5

Using the method of Example 4, the following compounds were obtained.

N-{2(S)-{2-(1,2,3,4-tetrahydro)naphthoylamino}-4-methylpentyl}-N-( 1-naphthylmethyl)-glycyl-methionine methyl ester
Anal. Calcd. for $C_{36}H_{47}N_3O_4S$•0.25 EtOAc C, 69.45 : H, 7.72: N, 6.57 C, 69.24 :H, 7.65 :N, 6.64
Fab mass spectrum m/z=618 (M+1)

N-{2(S)-[1,2,3,4-tetrahydro)naphthoylamino]-4-methylpentyl}-N-( 1-naphthylmethyl-glycyl-methionine methyl ester
Anal. Calcd. for $C_{36}H_{47}N_3O_4S$•0.50 EtOAc C, 68.95: H, 7.77 :N, 6.35 C, 69.07: H, 7.71 :N, 6.37
Fab mass spectrum m/z=618 (M+1)

N-{2(S)-[4-(4-hydroxyphenyl )butanoylamino]-4-methylpentyl}-N-( 1-naphthylmethyl)-glycyl-methionine methyl ester
Anal. Calcd for C35H47N3O05S•0.3 TFA•0.5 $H_2O$: C, 57.17; H, 6.20; N, 5.26. Found: C, 57.16; H, 6.17; N, 5.50.

N-{2(S)-[4-(4-aminophenyl)butanoylamino]-4-methylpentyl}-N-( 1-naphthylmethyl)-glycyl-methionine methyl ester
Anal. Calcd for C35H48N4O4S•2.25 TFA •0.25 $H_2O$: C, 53.79; H, 5.80; N, 6.35. Found: C, 53.70; H, 5.78; N, 6.56.

N-{2(S)-[2-benzylbenzoylamino]-4-methylpentyl}-N-(1-naphthylmethyl)-glycyl-methionine methyl ester FAB MS m/z=655 (M+1).

N-{2(S)-[(2-benzoylphenyl)acetylamino]-4-methylpentyl}-N-( 1-naphthylmethyl)-glycyl-methionine methyl ester
Anal. Calcd for C40H48N3O5S•0.5 EtOAc: C, 69.39; H, 7.21; N, 5.78. Found: C, 69.15; H, 6.99: N, 5.95.

N-{2(S)-[(2-benzoylphenyl)acetylamino]-4-methylpentyl}-N-( 1-naphthylmethyl)-glycyl-methionine methyl ester
Anal. Calcd for C40H50N3O4S•0.5 EtOAc: C, 70.75; H, 7.63; N, 5.89. Found: C, 70.87; H, 7.34: N, 6.21.

N-{2(S)-[(4-benzylphenyl)acetylamino]-4-methylpentyl}-N-( 1-naphthylmethyl)-glycyl-methionine methyl ester
Anal. Calcd for C40H50N3O4S•0.75 EtOAc: C, 70.26; H, 7.68; N, 5.72. Found: C, 70.14; H, 7.28; N, 5.89.

N-{2(S)-[(3-benzoylphenyl)acetylamino]-4-methylpentyl}-N-( 1-naphthylmethyl)-glycyl-methionine methyl ester
Anal. Calcd for C40H48N3O5S•0.3 EtOAc: C, 69.76; H, 7.16; N, 5.92. Found: C, 69.76; H, 6.95: N, 6.07.

Example 6

The following compounds were prepared using the procedure described for Example 1, Step G but substituting the methyl ester used therein with the corresponding methyl ester from Examples 4 and 5.

N-{2(S)-[4-(4-methoxyphenyl)-4-oxobutanoylamino]-4-methylpentyl}-N-(1-naphthylmethyl)-glycyl-methionine
This compound was prepared by in situ hydrolysis of the corresponding methyl ester.

N-{2(S)-[2-(1,2,3,4-tetraydro)naphthoylamino]- 4-methylpentyl}-N(1-naphthylmethyl)-glycyl-methionine
Anal. Calcd. for $C_{35}H_{45}N_3O_4S$•0.8 $H_2O$ C, 67.99: H, 7.60: N, 6.80 C, 67.99:1t, 7.35 : N, 6.73

N-{2(S)-[1-(1,2,3,4-tetrahydro)naphthoylamino]- 4-methylpentyl}-N-(1-naphthylmethyl)-glycyl-methionine Anal. Calcd. for $C_{35}H_{45}N_3O_4S \cdot 0.8\ H_2O$ C, 67.99: H, 7.60 : N, 6.80 C, 67.60:1t, 7.32 : N, 6.82

N-{2(S)-[4-(4-nitrophenyl)butanoylamino]- 4-methylpentyl}-N-(1-naphthylmethyl)-glycyl-methionine Anal. Calcd for $C_{34}H_{44}N_4O_6S \cdot 0.75$ EtOAc $\cdot 0.25\ H_2O$: C, 62.82; H, 7.20; N, 7.92. Found: C, 62.84; H, 7.03: N, 7.83.

N-{2(S)-[4-(4-hydroxyphenyl)butanoylamino]-4-methylpentyl}-N-( 1-naphthylmethyl)-glycyl-methionine Anal. Calcd for C34H45N3O5S•0.1 EtOAc •0.80 H₂O: C, 65.47; H, 7.57; N, 6.66. Found: C, 65.46; H, 7.26; N, 6.66.

N-{2(S)-[(3-benzoylphenyl)acetylamino]-4-methylpentyl}-N-( 1-naphthylmethyl)-glycyl-methionine Anal. Calcd for C39H46N3O5S•0.5 EtOAc•0.35 $H_{20}$: C, 68.46; H, 7.11; N, 5.84. Found: C, (68.47; H, 6.83; N, 5.81.

N-{2(S)-[4-(4-aminophenyl)butanoylamino]- 4-methylpentyl}-N-(1-naphthylmethyl)-glycyl-methionine This compound was prepared by in situ hydrolysis of the corresponding methyl ester.

N-{2(S)-[2-benzylbenzoylamino]-4-methylpentyl}-N-(1-naphthylmethyl)-glycyl-methionine Anal. Calcd for $C_{38}H_{46}N_3O_4S \cdot 0.5\ H_2O$: C, 70.23; H, 7.29; N, 6.47. Found: C, 70.05; H, 7.02: N, 6.49.

N-{2(S)-[(2-benzoylphenyl)acetylamino]-4-methylpentyl}-N-( 1-naphthylmethyl)-glycyl-methionine Anal. Calcd for $C_{39}H_{46}N_3O_5S \cdot 0.45\ H_2O$: C, 69.19; H, 6.98; N, 6.21. Found: C, 69.23; H, 6.73: N, 6.09.

N-{2(S)-[(2-benzylphenyl)acetylamino]-4-methylpentyl}-N-( 1-naphthylmethyl)-glycyl-methionine $^1$H NMR was consistent with the named structure.

N-{2(S)-[(4-benzylphenyl)acetylamino]-4-methylpentyl}-N-( 1-naphthylmethyl)-glycyl-methionine Anal. Calcd for $C_{39}H_{48}N_3O_4S \cdot 0.1$ EtOAc$\cdot 0.35\ H_2O$: C, 70.62; H, 7.45; N, 6.27. Found: C, 70.64; H, 7.25; N, 6.18.

EXAMPLE 32

In vitro inhibition of ras farnesyl transferase

Assays of farnesyl-protein transferase. Partially purified bovine FPTase and Ras peptides (Ras-CVLS, Ras-CVIM and RAS-CAIL) were prepared as describe :1 by Schaber et al., *J. Biol. Chem.* 265:14701–14704 (1990)., Pompliano, et al., *Biochemistry* 31:3800 (1992) and Gibbs et al., *PNAS U.S.A.* 86:6630–6634 (1989). Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31 ° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <10 µM.

EXAMPLE 32

In vivo ras farnesylation assay.

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1mM DTT/10 mg/ml aprotinen/2 mg/ml leupeptin/2 mg/ml antipain/0.5 mM PMSF) and the lysates cleared by centrifugation at 100,000 x g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 33

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3 % top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures were seeded and comparisons are made.

What is claimed is:

1. A compound which inhibits Ras farnesyl-transferase having the formula I:

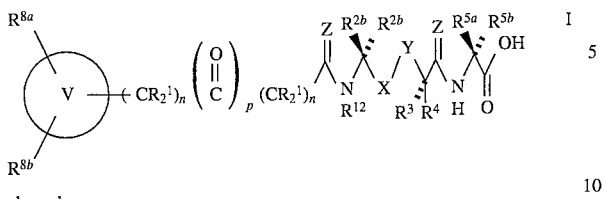

wherein:

$R^1$ is hydrogen, $C_1$–$C_6$ alkyl or aryl;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$,—$N(R^9)_2$, $R^{10}C(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substitute or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

$R^{5a}$ and $R^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^9)$—;

X-Y is

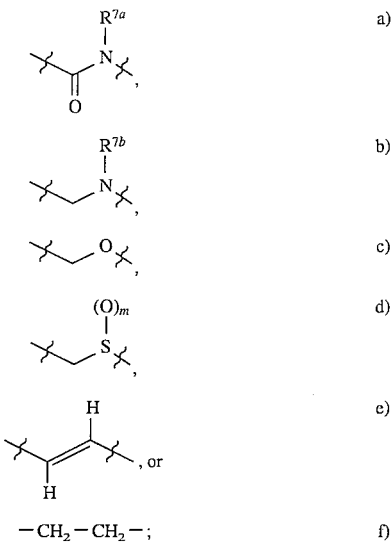

—$CH_2$—$CH_2$—;  f)

$R^{7a}$ is selected from
  a) hydrogen,
  b) unsubstituted or substituted aryl,
  c) unsubstituted or substituted heterocycle,
  d) unsubstituted or substituted cycloalkyl, and
  e) $C_1$–$C_6$ alkyl substituted with hydrogen or an unsubstituted or substituted group selected from aryl, heterocycle and cycloalkyl;

$R^{7b}$ is selected from
  a) hydrogen,
  b) unsubstituted or substituted aryl,
  c) unsubstituted or substituted heterocycle,
  d) unsubstituted or substituted cycloalkyl,
  e) $C_1$–$C_6$ alkyl substituted with hydrogen or an unsubstituted or substituted group selected from aryl, heterocycle and cycloalkyl,
  f) a carbonyl group which is bonded to an unsubstituted or substituted group selected from aryl, heterocycle, cycloalkyl mid $C_1$–$C_6$ alkyl substituted with hydrogen or an unsubstituted or substituted group selected from aryl, heterocycle and cycloalkyl, and
  g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

is aryl or 1,2,3,4-tetrahydronaphthyl;
Z is independently $H_2$ or O;
m is 0, 1 or 2;
n is independently 0 to 4;
p is 0 or 1; and
s is 4 or 5;
or a pharmaceutically acceptable salt thereof.

2. A prodrug of a compound of claim 1 having the formula II:

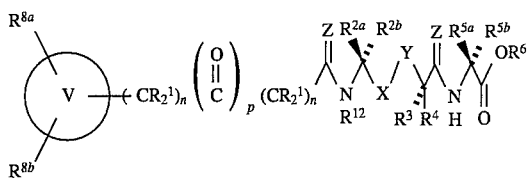

wherein:
$R^1$ is hydrogen, $C_1$–$C_6$ alkyl or aryl;
$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;
$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;
$R^{5a}$ and $R^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloallyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^9)$—;

$R^6$ is
  a) substituted or unsubstituted $C_1$–$C_8$ alkyl, wherein the substituent on the alkyl is selected from:
    1) aryl,
    2) heterocycle,
    3) —$N(R^{10})_2$,
    4) —$OR^9$, or b) 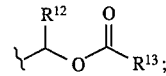

X-Y is

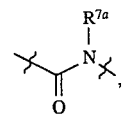 a)

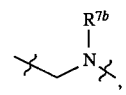 b)

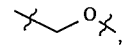 c)

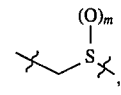 d)

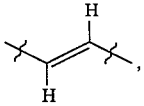, or e)

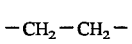 f)

$R^{7a}$ is selected from
  a) hydrogen,
  b) unsubstituted or substituted aryl,
  c) unsubstituted or substitute heterocycle,
  d) unsubstituted or substituted cycloalkyl, and
  e) $C_1$–$C_6$ alkyl substituted with hydrogen or an unsubstituted or substituted group selected from aryl, heterocycle and cycloalkyl;

$R^{7b}$ is selected from
  a) hydrogen,
  b) unsubstituted or substituted aryl,
  c) unsubstituted or substituted heterocycle,
  d) unsubstituted or substituted cycloalkyl,
  e) $C_1$–$C_6$ alkyl substituted with hydrogen or an unsubstituted or substituted group selected from aryl, heterocycle and cycloalkyl,
  f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
  g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

$R^{13}$ is $C_1$–$C_6$ alkyl;

is aryl or 1,2,3,4-tetrahydronaphthyl;

Z is independently $H_2$ or O;

m is 0, 1 or 2;

n is independently 0 to 4;

p is 0 or 1; and s is 4 or 5;

or a pharmaceutically acceptable salt thereof.

3. A compound which inhibits Ras farnesyl-transferase having the formula III:

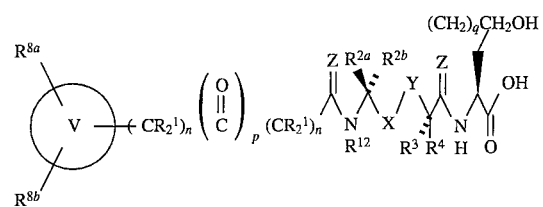

wherein:

$R^1$ is hydrogen, $C_1$–$C_6$ alkyl or aryl;

$R^{2a}$ and $R^{2b}$ are independently selected from:

a) a side chain of a naturally occurring amino acid, b) an oxidized form of a side chain of a naturally occurring amino acid which is:
  i) methionine sulfoxide, or
  ii) methionine sulfone, and c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:

a) a side chain of a naturally occurring amino acid, b) an oxidized form of a side chain of a naturally occurring amino acid which is:
  i) methionine sulfoxide, or
  ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

X-Y is

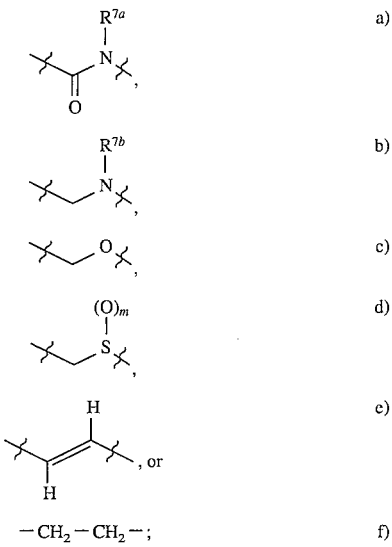

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

$R^{7b}$ is selected from a) hydrogen, b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

is aryl or 1,2,3,4-tetrahydronaphthyl;
Z is independently $H_2$ or O;
m is 0, 1 or 2;
n is independently 0 to 4;
p is 0 or 1;
q is 0, 1 or 2; and
s is 4 or 5;
or a pharmaceutically acceptable salt thereof.

4. The compound according to claim 1 having the formula I:

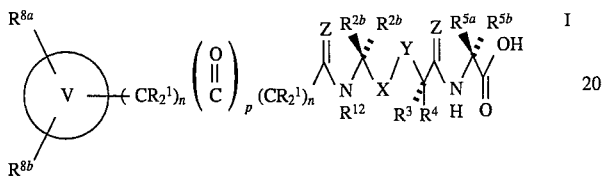

wherein:
$R^1$ is hydrogen, $C_1$–$C_6$ alkyl or aryl;
$R^{2a}$ is selected from:
  a) a side chain of a naturally occurring amino acid, wherein the amino acid is selected from alanine, leucine, isoleucine and valine; and
  b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  c) $C_1$–$C_6$ alkyl substituted with an unsubstituted or substituted group selected from aryl, heterocycle and $C_3$–$C_{10}$ cycloalkyl; and
$R^{2b}$ is hydrogen or $C_1$–$C_6$ alkyl; or
$R^{2a}$ and $R^{2b}$ are combined to form —$(CH_2)_s$—;
$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$&14 $C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;
$R^{5a}$ is selected from:
  a) a side chain of a naturally occurring amino acid, wherein the amino acid is selected from methionine and glutamine,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_1$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR_9$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;
$R^{5b}$ is selected from:
  a) hydrogen, and
  b) $C_1$–$C_3$ alkyl; or
X-Y is

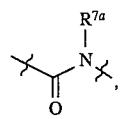 a)

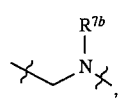 b)

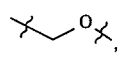 c)

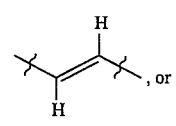 d)

—$CH_2$—$CH_2$—; e)

$R^{7a}$ is selected from
  a) hydrogen,
  b) unsubstituted or substituted aryl,
  c) unsubstituted or substituted heterocycle,
  d) unsubstituted or substituted cycloalkyl, and
  e) $C_1$–$C_6$ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;
$R^{7b}$ is selected from
  a) hydrogen,
  b) unsubstituted or substituted aryl,
  c) unsubstituted or substituted heterocycle,
  d) unsubstituted or substituted cycloalkyl,
  e) $C_1$–$C_6$ alkyl substituted with hydrogen or an unsubstituted or substituted group selected from aryl, heterocycle and cycloalkyl,
  f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
  g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{8a}$ and $R^{8b}$ are independently selected from: hydrogen, F, Cl, Br, $NO_2$, R11—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

(V)

is aryl or 1,2,3,4-tetrahydronaphthyl;

Z is independently $H_2$ or O;

m is 0, 1 or 2;

n is independently 0 to 4:

p is 0 or 1; and s is 4 or 5;

or a pharmaceutically acceptable salt thereof.

5. The compound according to claim 2 having the formula II:

$$\text{II}$$

wherein:

$R^1$ is hydrogen, $C_1$–$C_6$ alkyl or aryl;

$R^{2a}$ is selected from:

a) a side chain of a naturally occurring amino acid, wherein the amino acid is selected from alanine, leucine, isoleucine and valine;

b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and c) $C_1$–$C_6$ alkyl substituted with an unsubstituted or substituted group selected from aryl, heterocycle and $C_3$–$C_{10}$ cycloalkyl; and $R^2b$ is hydrogen or $C_1$–$C_{10}$ alkyl; or $R^{2a}$ and $R^{2b}$ are combined to form —$(CH_2)_s$—;

$R^3$ and $R^4$ are independently selected from:

a) a side chain of a naturally occurring amino acid, b) an oxidized form of a side chain of a naturally occurring amino acid which is:
 i) methionine sulfoxide, or
 ii) methionine sulfone, c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl;

$R^{5a}$ is selected from:

a) a side chain of a naturally occurring amino acid, wherein the amino acid is selected from methionine and glutamine, b) an oxidized form of a side chain of a naturally occurring amino acid which is:
 i) methionine sulfoxide, or
 ii) methionine sulfone, c) substituted or unsubstituted $C_1$–$C_{10}$ alkyl, $C_1$–$C_{20}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl;

$R^{5b}$ is selected from:

a) hydrogen, and b) $C_1$–$C_3$ alkyl; or $R^6$ is a) substituted or unsubstituted $C_1$–$C_8$ alkyl, wherein the substituent on the alkyl is selected from:
 1) aryl,
 2) heterocycle,
 3) —$N(R^{10})_2$,
 4) —$OR^9$, or b)

$$\text{b)}$$

X-Y is a)

b)

c)

d)

e) —$CH_2$—$CH_2$—;

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl:

$R^{7b}$ is selected from a) hydrogen, b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{8a}$ and $R^{8b}$ are independently selected from: hydrogen, F, Cl, Br, $NO_2$, $R^{11}O$—, $R^{10}S(O)_m$—, CN, $R^9C(O)NR^9$—, $(R^9)_2N$—$C(NR^9)$—, $R^9C(O)$—, $R^9OC(O)$—, $N_3$, —$N(R^9)_2$, $R^{10}OC(O)NR^9$—, $C_1$–$C_{20}$ alkyl, aryl, heterocycle or $C_1$–$C_{20}$ alkyl substituted with aryl or heterocycle;

$R^9$ is independently selected from hydrogen, $C_1$–$C_6$ alkyl and aryl;

$R^{10}$ is independently selected from $C_1$–$C_6$ alkyl and aryl;

$R^{11}$ is independently selected from hydrogen, $C_1$–$C_6$ alkyl and aryl, provided $R^{11}$ is $C_1$–$C_6$ alkyl when n is 0;

$R^{12}$ is independently hydrogen or $C_1$–$C_6$ alkyl;

$R^{13}$ is $C_1$–$C_6$ alkyl;

is aryl or 1,2,3,4-tetrahydronaphthyl;
Z is independently $H_2$ or O;
m is 0, 1 or 2;
n is independently 0 to 4;
p is 0 or 1; and
s is 4 or 5;
or a pharmaceutically acceptable salt thereof.

6. The compound according to claim 3 having the formula III:

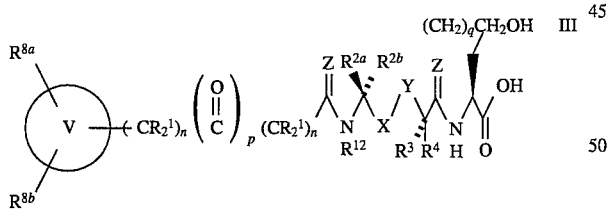

$R^1$ is hydrogen, $C_1$–$C_6$ alkyl or aryl;
$R^{2a}$ is selected from:

a) a side chain of a naturally occurring amino acid, wherein the amino acid is selected from alanine, leucine, isoleucine and valine; and b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ aryl substituted with an unsubstituted or substituted group selected from aryl, heterocycle and $C_3$–$C_{10}$ cycloalkyl; and $R^{2b}$ is hydrogen or $C_1$–$C_4$ alkyl; or
$R^{2a}$ and $R^{2b}$ are combined to form —$(CH_2)_s$—;
$R^3$ and $R^4$ are independently selected from:

a) a side chain of a naturally occurring amino acid, b) an oxidized form of a side chain of a naturally occurring amino acid which is:
  i) methionine sulfoxide, or
  ii) methionine sulfone, c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, $NO_2$, $R^9O$—, $R^{10}S(O)_m$—, $R^9C(O)NR^9$—, CN, $(R^9)_2N$—$C(NR^9)$—, $R^9C(O)$—, $R^9OC(O)$—, $N_3$, —$N(R^9)_2$, $R^{10}OC(O)NR^9$— and $C_1$–$C_{20}$ alkyl, and d) $C_1$–$C_6$ alkyl substituted with an unsubstituted or substituted group selected from aryl, heterocycle and $C_3C_{10}$ cycloalkyl;

X-Y is

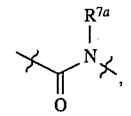 a)

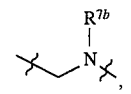 b)

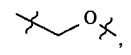 c)

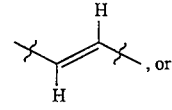 d)

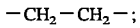 e)

$-CH_2-CH_2-$;

$R^{7a}$ is selected from
a) hydrogen,
b) unsubstituted or substituted aryl,
c) unsubstituted or substituted heterocycle,
d) unsubstituted or substituted cycloalkyl, and
e) $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{8a}$ and $R^{8b}$ are independently selected from: hydrogen, F, Cl, Br, $NO_2$, $R^{11}O—$, $R^{10}S(O)_m—$, CN, $R^9C(O)NR^9—$, $(R^9)_2N—C(NR^9)—$, $R^9C(O)—$, $R^9OC(O)—$, $N_3$, $—N(R^9)_2$, $R^{10}OC(O)NR^9—$, $C_1–C_{20}$ alkyl, aryl, heterocycle or $C_1–C_{20}$ alkyl substituted with aryl or heterocycle;

$R^9$ is independently selected from hydrogen, $C_1–C_6$ alkyl and aryl;

$R^{10}$ is independently selected from $C_1–C_6$ alkyl and aryl;

$R^{11}$ is independently selected from hydrogen, $C_1–C_6$ alkyl and aryl, provided $R^{11}$ is $C_1–C_6$ alkyl when n is 0;

$R^{12}$ is independently hydrogen or $C_1–C_6$ alkyl;

is aryl or 1,2,3,4-tetrahydronaphthyl;
Z is independently $H_2$ or O;
m is 0, 1 or 2;
n is independently 0 to 4;
p is 0 or 1;
q is 0, 1 or 2; and
s is 4 or 5;
or a pharmaceutically acceptable salt thereof.

7. A compound which inhibits farnesyl-protein transferase which is:

N-{2(S)-[4-(4-nitrophenyl)butanoylamino]-3(S)-methylpentyl}-N-( 1-naphthylmethyl)-glycyl-methionine methyl ester N-{2(S)-[5-phenylpentanoylamino]-3(S)-methylpentyl}-N-( 1-naphthylmethyl-glycyl-methionine methyl ester N-{2(S)-[4-phenylbenzoylamino]-3(S)-methylpentyl}-N-(1-naphthylmethyl-glycyl-methionine methyl ester N-{2(S)-[5-(2,4-dinitrophenyl)pentanoylamino]- 3(S)-methylpentyl}-N-(1-naphthylmethyl)-glycyl-methionine methyl ester N-{2(S)-[4-nitrobenzoylamino]-3(S)-methylpentyl}-N-(1-naphthylmethyl)-glycyl-methionine methyl ester N-{2(S)-[3-(3-indolyl)propanoylamino}-3 (S)-methylpentyl}-N-( 1-naphthylmethyl)-glycyl-methionine methyl ester N-{2(S)-[3-(1-indolyl)propanoylamino}-3(S)-methylpentyl}-N-( 1-naphthylmethyl)-glycyl-methionine methyl ester N-{2(S)-[4-(4-methoxyphenyl)-4-oxobutanoylamino]-4-methylpentyl}-N-(1-naphthylmethyl-glycyl-methionine methyl ester N-{2(S)-{2-(1,2,3,4-tetrahydro)naphthoylamino}- 4-methylpentyl}-N(1-naphthylmethyl)-glycyl-methionine methyl ester N-{2(S)-[1-(1,2,3,4-tetrahydro)naphthoylamino]-4-methylpentyl}-N-( 1-naphthylmethyl-glycyl-methionine methyl ester N-{2(S)-[4-(4-hydroxyphenyl)butanoylamino]-4-methylpentyl}-N-( 1-naphthylmethyl)-glycyl-methionine methyl ester N-{2(S)-[4-(4-aminophenyl)butanoylamino]-4-methylpentyl}-N-( 1-naphthylmethyl)-glycyl-methionine methyl ester N-{2(S)-[2-benzylbenzoylamino]-4-methylpentyl}-N-(1-naphthylmethyl)-glycyl-methionine methyl ester N-{2(S)-[(2-benzoylphenyl)acetylamino]-4-methylpentyl}-N-( 1-naphthylmethyl)-glycyl-methionine methyl ester N-{2(S)-[(2-benzylphenyl)acetylamino]-4-methylpentyl}-N-( 1-naphthylmethyl)-glycyl-methionine methyl ester N-{2(S)-[(4-benzylphenyl)acetylamino]-4-methylpentyl}-N-( 1-naphthylmethyl)-glycyl-methionine methyl ester N-{2(S)-[(3-benzoylphenyl)acetylamino]-4-methylpentyl}-N-( 1-naphthylmethyl)-glycyl-methionine methyl ester N-{2(S)-[4-(4-nitrophenyl)butanoylamino]-3(S)-methylpentyl}-N-( 1-naphthylmethyl)-glycyl-methionine N-{2(S)-[5-phenylpentanoylamino]-3(S)-methylpentyl}-N-( 1-naphthylmethyl)-glycyl-methionine N-{2(S)-[4-phenylbenzoylamino]-3(S)-methylpentyl}-N-(1-naphthylmethyl)-glycyl-methionine N-{2(S)-[5-(2,4-dinitrophenyl)pentanoylamino]- 3(S)-methylpentyl}-N-(1-naphthylmethyl)-glycyl-methionine N-{2(S)-[4-nitrobenzoylamino]-3(S)-methylpentyl}-N-(1-naphthylmethyl)-glycyl-methionine N-{2(S)-[3-(3-indolyl)propanoylamino]- 3(S)-methylpentyl}-N-(1-naphthylmethyl)-glycyl-methionine N-{2(S)-[3-(1-indolyl)propanoylamino]- 3(S)-methylpentyl}-N-(1-naphthylmethyl)-glycyl-methionine N-{2(S)-[4-(4-methoxyphenyl)-4-oxobutanoylamino]- 4methylpentyl}-N-(1-naphthylmethyl)-glycyl-methionine N-{2(S)-[2-(1,2,3,4-tetrahydro)naphthoylamino]- 4-methylpentyl}-N-(1-naphthylmethyl)-glycyl-methionine N-{2(S)-[1-(1,2,3,4-tetrahydro)naphthoylamino]- 4-methylpentyl}-N(1-naphthylmethyl)-glycyl-methionine N-{2(S)-[4-(4-nitrophenyl)butanoylamino]- 4-methylpentyl}-N-(1-naphthylmethyl)-glycyl-methionine N-{2(S)-[4-(4-hydroxyphenyl)butanoylamino]- 4-methylpentyl}-N-(1-naphthylmethyl)-glycyl-methionine N-{2(S)-[(3-benzoylphenyl)acetylamino]-4-methylpentyl}-N-( 1-naphthylmethyl)-glycyl-methionine N-{2(S)-[4-(4-aminophenyl)butanoylamino]-4-methylpentyl}-N-( 1-naphthylmethyl)-glycyl-methionine N-{2(S)-[2-benzylbenzoylamino]-4-methylpentyl}-N-( 1-naphthylmethyl)-glycyl-methionine N-{2(S)-[(2-benzoylphenyl)acetylamino]-4-methylpentyl}-N-( 1-naphthylmethyl)-glycyl-methionine N-{2(S)-[(2-benzylphenyl)acetylamino]-4-methylpentyl}-N-( 1-naphthylmethyl)-glycyl-methionine or N-{2(S)-[(4-benzylphenyl)acetylamino]-4-methylpentyl}-N-( 1-naphthylmethyl)-glycyl-methionine or a pharmaceutically acceptable salt thereof.

8. A compound which inhibits farnesyl-protein transferase which is:

N-{2(S)-[4-(4-nitrophenyl)butanoylamino]-3(S)-methylpentyl}-N-( 1-naphthylmethyl)-glycyl-methionine

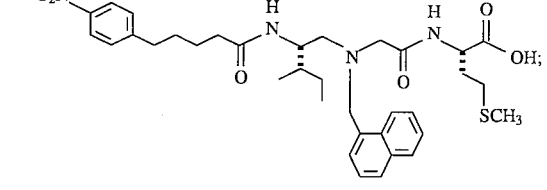

or a pharmaceutically acceptable salt thereof.

9. A compound which inhibits farnesyl-protein transferase which is:

N-{2(S)-[4-(4-nitrophenyl)butanoylamino]-3(S)-methylpentyl}-N-( 1-naphthylmethyl)-glycyl-methionine methyl ester

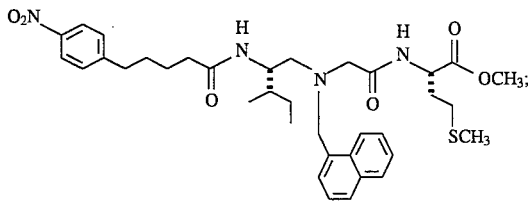

or a pharmaceutically acceptable salt thereof.

10. A compound which inhibits farnesyl-protein transferase which is:
N-{2(S)-[5-(2,4-dinitrophenyl)pentanoylamino]- 3(S)-methylpentyl}-N-(1-naphthylmethyl)-glycyl-methionine

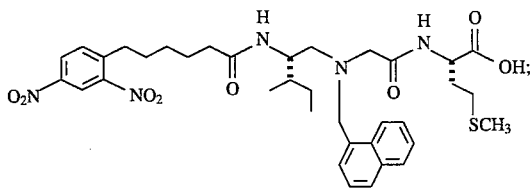

or the pharmaceutically acceptable salt thereof.

11. A compound which inhibits farnesyl-protein transferase which is:
N-{2(S)-[5-(2,4-dinitrophenyl)pentanoylamino]-3(S)-methylpentyl}-N( 1-naphthylmethyl)-glycyl-methionine methyl ester

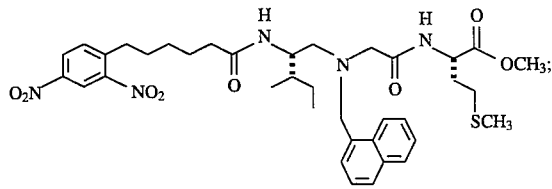

or a pharmaceutically acceptable salt thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 2.

14. A pharmaceutical composition comprising a pharmaceutical carrier, and dispersed therein, a therapeutically effective amount of a compound of claim 3.

15. A pharmaceutical composition comprising a pharmaceutical carrier, and dispersed therein, a therapeutically effective amount of a compound of claim 7.

16. A method for inhibiting farnesylation of Ras protein which comprises administering to a mammal in need thereof a therapeutically effective amount of the composition of claim 12.

17. A method for inhibiting farnesylation of Ras protein which comprises administering to a mammal in need thereof a therapeutically effective amount of the composition of claim 13.

18. A method for inhibiting farnesylation of Ras protein which comprises administering to a mammal in need thereof a therapeutically effective amount of the composition of claim 14.

19. A method for inhibiting farnesylation of Ras protein which comprises administering to a mammal in need thereof a therapeutically effective amount of the composition of claim 15.

20. A method for treating cancer which comprises administering to a mammal in need thereof a therapeutically effective amount of a composition of claim 12.

21. A method for treating cancer which comprises administering to a mammal in need thereof a therapeutically effective amount of a composition of claim 13.

22. A method for treating cancer which comprises administering to a mammal in need thereof a therapeutically effective amount of a composition of claim 14.

23. A method for treating cancer which comprises administering to a mammal in need thereof a therapeutically effective amount of a composition of claim 15.

\* \* \* \* \*